(12) United States Patent
Ruan

(10) Patent No.: US 11,639,356 B2
(45) Date of Patent: May 2, 2023

(54) SUBSTITUTED IMIDAZO[1,2-A]PYRAZINES AND PYRAZINO[1,2-A]PYRIMIDINES AS TOPICAL AGENTS FOR DERMATOLOGICAL APPLICATIONS

(71) Applicant: Genesis Molecular Technologies, Inc., Austin, TX (US)

(72) Inventor: Fuqiang Ruan, Bellevue, WA (US)

(73) Assignee: Genesis Molecular Technologies, Inc., Austin, TX (US)

( * ) Notice: Subject to any disclaimer, the term of this patent is extended or adjusted under 35 U.S.C. 154(b) by 0 days.

(21) Appl. No.: 17/492,514

(22) Filed: Oct. 1, 2021

(65) Prior Publication Data
US 2022/0106320 A1    Apr. 7, 2022

Related U.S. Application Data

(60) Provisional application No. 63/087,670, filed on Oct. 5, 2020.

(51) Int. Cl.
| | | |
|---|---|---|
| A61K 31/4985 | (2006.01) | |
| C07D 487/04 | (2006.01) | |
| A61Q 19/00 | (2006.01) | |
| A61K 8/49 | (2006.01) | |

(52) U.S. Cl.
CPC .......... *C07D 487/04* (2013.01); *A61K 8/4953* (2013.01); *A61Q 19/00* (2013.01)

(58) Field of Classification Search
CPC .......................... A61K 31/4985; C07D 487/04
USPC ............................................ 514/249; 544/350
See application file for complete search history.

(56) References Cited

U.S. PATENT DOCUMENTS

| | | |
|---|---|---|
| 2008/0009500 A1 | 1/2008 | Kahn |
| 2010/0069333 A1 | 3/2010 | Kahn |

FOREIGN PATENT DOCUMENTS

| | | |
|---|---|---|
| WO | 2011/090317 A2 | 7/2011 |

OTHER PUBLICATIONS

Emami, K.H., et al., "A Small Molecule Inhibitor of β-Catenin/CREB-Binding Protein Transcription," Proceedings of the National Academy of Science U.S.A. 101(34):12682-12687, Aug. 24, 2004.

Matsuda-Hirose, H., et al., "Selective Inhibition of β-Catenin/Co-Activator Cyclic AMP Response Element-Binding Protein-Dependent Signaling Prevents the Emergence of Hapten-Induced Atopic Dermatitis-Like Dermatitis," Ann Dermatol, 31(6):631-619, 2019.

Veltri, A., et al., "Concise Review: Wnt Signaling Pathways in Skin Development and Epidermal Stem Cells," Stem Cells 36:22-35, 2018.

International Search Report and Written Opinion dated Jan. 6, 2022, issued in International Patent Application Mo. PCT/US2021/053176, filed Oct. 21, 2021, 7 pages.

*Primary Examiner* — Douglas M Willis
(74) *Attorney, Agent, or Firm* — Barry L. Davison; Davis Wright Tremaine LLP

(57) ABSTRACT

Provided are compounds of formula (I):

(I)

or cosmeceutically acceptable or pharmaceutically acceptable salts thereof. Additionally provided are cosmeceutical and/or pharmaceutical compositions comprising the compounds of formula (I), or the cosmeceutically acceptable or pharmaceutically acceptable salts thereof. Also provided are therapeutic and/or cosmetic methods using the cosmeceutical and/or pharmaceutical compositions comprising the compounds of formula (I), or the cosmeceutically acceptable or pharmaceutically acceptable salts thereof, for modulating cyclic adenosine monophosphate response element binding (CREB)-binding protein (CBP)/β-catenin mediated signaling in treating skin related diseases, conditions, or disorders mediated by aberrant CBP/β-catenin signaling and cosmetic methods for treating skin conditions mediated by aberrant CBP/β-catenin signaling.

25 Claims, 3 Drawing Sheets
(1 of 3 Drawing Sheet(s) Filed in Color)

(a) NP-002 in a solid form (0 day)

(b) NP-002 in a solid form (after 4 days at rt)

(c) NP-002 in CH3CN and CH3OH (after 4 days at rt)

Baseline 8 weeks

SUBSTITUTED IMIDAZO[1,2-A]PYRAZINES AND PYRAZINO[1,2-A]PYRIMIDINES AS TOPICAL AGENTS FOR DERMATOLOGICAL APPLICATIONS

CROSS-REFERENCE TO RELATED APPLICATION

This application claims the benefit of priority to U.S. Provisional Patent Application No. 63/087,670, filed Oct. 5, 2020, which is hereby incorporated by reference in its entirety.

FIELD OF THE INVENTION

The present invention relates generally to modulation of the Wnt/β-catenin pathway in mammalian (both human and non-human) cells and tissues, and more particularly to novel CREB binding protein (CBP)/β-catenin inhibitors and prodrugs thereof, cosmetic, and therapeutic uses thereof (e.g., in dermatological applications), and methods of making the disclosed exemplary compounds.

BACKGROUND OF THE INVENTION

Skin is the largest organ of human body, and along with hair and nails, skin acts as a boundary between the body and the external environment, protecting the body against pathogens and excessive water loss. Skin is also critical for insulation, temperature regulation, sensation, and the synthesis of molecules such as vitamin D. Skin and hair are additionally important in self-image and self-esteem. Skin care and dermatological treatments, including for healing of wounds, ulcers and burns, and treatment of acne, atopic dermatitis, psoriasis, alopecia, as well as for providing cosmetic, anti-aging effects, are thus needed or desired to improve health and appearance of the outer epidermis, the underlying dermis, and other tissues.

Wounds, ulcers and burns, which are either injury induced (e.g., cuts, abrasions either from injury or treatments such as laser mediated dermabrasion, blisters) or surgically induced (e.g., surgical incisions, ostomies) require localized treatment to remedy the affected area and to prevent further dermal damage. Most current medications for wounds, ulcers, burns, and skin diseases or disorders, however, merely focus on relief of the symptoms (e.g., inflammation), failing to target and address the underlying cause of the problem (see, e.g., Okur, M. E., et al., Asian J Pharm Sci. 2020; 10:661-684), and, therefore, do not speed the healing process. Similar challenges exist for cosmetic skin improvement and hair growth. For example, skin is the most visible reflection of human health and vitality, and wrinkles are an early sign of aging, which can have a negative effect on quality of life. Although Botox is one of the most common wrinkles treatments, it does not heal the skin and its use to reduce wrinkles must be under strict control due to its high toxicity (Benedetto, A. V., Clinics in dermatology. 1998; 16:129-139). Thus, novel safer and effective agents for skin care and dermatological treatments are needed.

As the largest organ in the human body, skin undergoes significant turnover and harbors multiple distinct stem and progenitor cells and yet routinely heals with a scar. The WNT signaling cascade has been implicated in skin development and maintenance (see: e.g., Weltri, A., et al., STEM CELLS. 2018; 36:22-35). Secreted Wnt proteins can stimulate multiple intracellular signaling pathways and act as growth factors that regulate diverse processes, including cell proliferation, differentiation, migration, and polarity. Among the Wnt stimulated pathways, Wnt/β-catenin signaling is known as an important regulatory pathway that governs developmental processes and fate choices during tissue morphogenesis. Wnt signaling is one of the major cues directing skin development and maintenance. Although Wnt signaling has been mainly implicated in HF (Hair Follicle) induction during skin development, it has also been recently shown to regulate epidermal stratification. In primary human keratinocytes, Wnt5a acts as an autocrine stimulus to promote extracellular calcium-induced keratinocyte differentiation by coupling with the Wnt/β-catenin pathway. Throughout life the skin epidermis is regularly renewed. Skin epidermal stem cells (SC), capable of self-renewal and differentiation, provide unlimited sources of cells to maintain tissue homeostasis, as well as to regenerate HFs and repair the epidermis after injury. Wnt signaling, including the Wnt/CBP/β-catenin pathway, is critical in all of these processes and Wnt dependent signaling plays crucial roles in the maintenance, activation, and fate determination of the SC populations. Thus, development of effective pharmacological Wnt/CBP/β-catenin antagonists and delivery strategies that result in an appropriately calibrated Wnt signaling modulation are needed to provide new and effective agents for treating skin related diseases and disorders, and effective cosmeceutical agents.

It is known that selective antagonists of the Wnt/CBP/β-catenin pathway (e.g., ICG-001) are extremely safe at effective levels based on animal toxicity studies and clinical studies, and it was found that CBP/β-catenin mediated transcription is critical for stem cell/progenitor cell maintenance and proliferation (Emami, K. H., et al., Proc. Natl. Acad. Sci. U.S.A. 2004; 101:12682-12687). However, in order to cross the predominant barrier function of stratum corneum in skin, a strategy for enhancing drug delivery (e.g., in a cream, lotion, ointment, spray, gel, powder, etc.) should be used in order to enhance topical delivery. In aspects of the present invention, esterified moieties (prodrugs) of the disclosed exemplary selective CBP/β-catenin inhibitors having enhanced lipophilicity are used to facilitate absorption or permeation across the stratum corneum into the viable epidermis and beyond. Such esterified drug moieties may be readily cleaved to release the corresponding non-esterified drug when exposed to skin microenvironments and the esterases contained within.

Additionally, a recent preclinical study indicated that ICG-001, a selective antagonist of the Wnt/CBP/β-catenin pathway, prevents the emergence of hapten-induced atopic dermatitis-like dermatitis (Matsuda-Hirose, H., et al., Ann Dermatol. 2019; 31(4):631-619). It is also known that humans can synthesize many of the fatty acids, with the exception of long chain fatty acids omega-3 (n-3) and omega-6 (n-6), which are called essential. Omega-3 fatty acids, represented by eicosapentaenoic (EPA) and docosahexaenoic acids (DHA), can reduce the severity of symptoms in many inflammatory skin diseases, including psoriasis (Balbas, G. M., et al., Clin. Cosmet. Investig. Dermatol. 2010; 28:615-26).

There is an unmet need in the art, and the disclosed CBP/β-catenin inhibitors, and the ester-containing analogs thereof (e.g., fatty acid esters, such as omega-3 and omega-6 fatty acid containing drug analogs, etc.) provide new and effective agents for treating skin related diseases or disorders, and aging related conditions, including for cosmetic purposes, preferably via topical delivery. Aspects of the present invention provide such compounds and salts thereof, along with pharmaceutical and/or cosmeceutical compositions comprising the compounds. Methods for synthesizing and using the compounds and compositions, both therapeutically and cosmeceutically, are also provided.

SUMMARY OF THE INVENTION

Aspects of the present invention may be described in the following clauses:

1. A compound of formula (I):

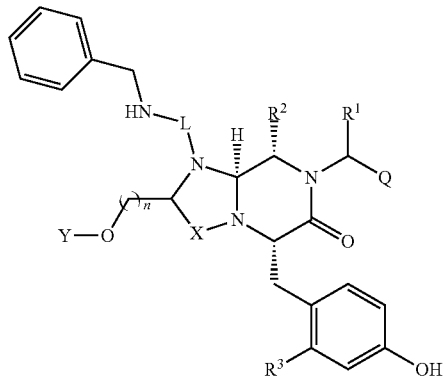

(I)

and pharmaceutically and/or cosmeceutically acceptable salts thereof, wherein:

$R^1$ and $R^2$ are independently selected from hydrogen or $CH_3$;

$R^3$ is hydrogen or deuterium;

Q is a phenyl group; a substituted phenyl group having one or more substituents wherein the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, optionally substituted $C_{1-4}$alkyl, optionally substituted $C_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, optionally substituted $C_{1-4}$alkylamino, optionally substituted $C_{1-4}$dialkylamino, halogen, perfluoro $C_{1-4}$alkyl, optionally substituted $C_{1-3}$-salkoxy, nitro, carboxy, cyano, sulfuryl, and hydroxyl group; or a optionally substituted bicyclic aryl group having 8 to 11 ring members, which may have 1 to 3 heteroatoms independently selected from nitrogen, oxygen or sulfur, L is —C(O)—, or —SO$_2$—;

X is —C(O)—, or —CH$_2$C(O)—;

n is 1 or 2; and

Y is hydrogen, or —C(O)R, wherein R is optionally substituted $C_1$-$C_{30}$ alkyl, optionally substituted $C_1$-$C_{30}$ alkenyl, or optionally substituted $C_1$-$C_{30}$alkylene.

2. The compound of clause 1, wherein the compound is of formula (Ia):

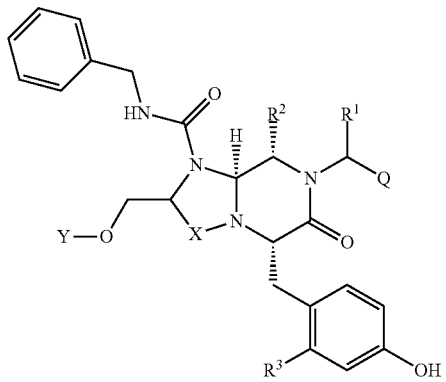

(Ia)

or a pharmaceutically and/or cosmeceutically acceptable salt thereof, wherein:

$R^1$, $R^2$, $R^3$, X, and Y are as defined in claim 1; and wherein

Q is selected from naphthyl, quinolinyl, isoquinolinyl, phthalazine, quinazoline, cinnoline, or naphthyridine.

3. The compound of clause 2, wherein the compound is of the formula (Ib):

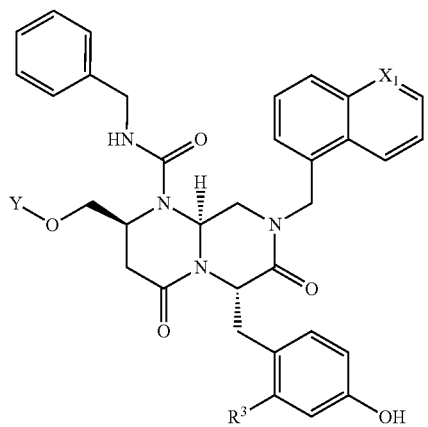

(Ib)

or a pharmaceutically and/or cosmeceutically acceptable salt thereof, wherein:

$R^3$ is defined in claim 2;

$X_1$ is N, or —CH—; and wherein

Y is hydrogen, or —C(O)R, wherein R is selected from:

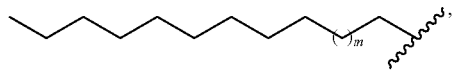

wherein m is 1 to 10,
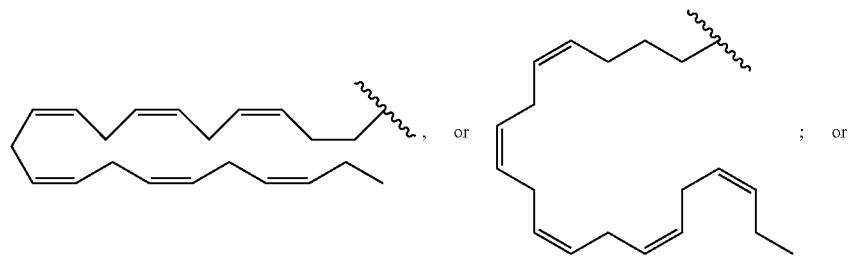
or
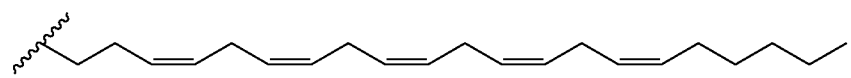
4. The compound of clause 2, wherein the compound is of the formula (Ic):
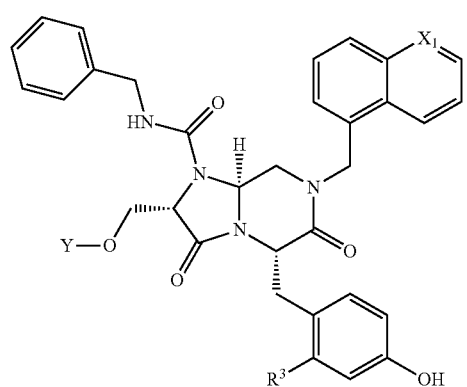
or a pharmaceutically and/or cosmeceutically acceptable salt thereof, wherein:
$R^3$ is defined as in claim 2;
$X_1$ is N, or —CH—, and wherein
Y is hydrogen, or —C(O)R, wherein R is selected from:
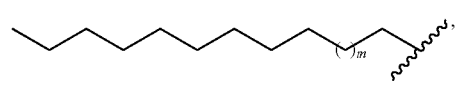
wherein m is 1 to 10,
or
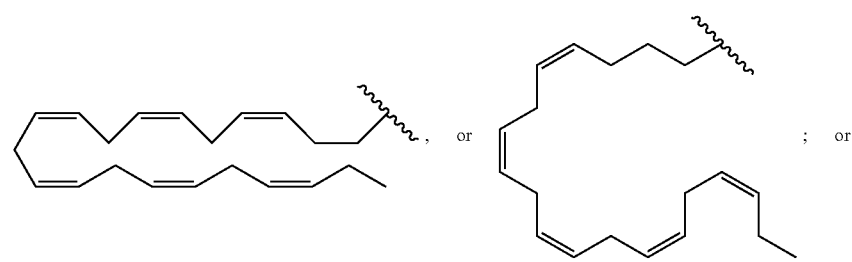
or
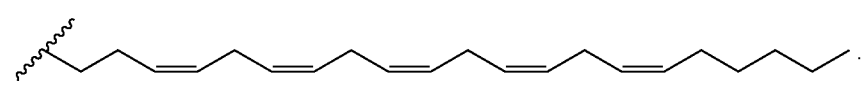

5. The compound of any one of clauses 1 to 4, or a pharmaceutically and/or cosmeceutically acceptable salt thereof, wherein the compound is:
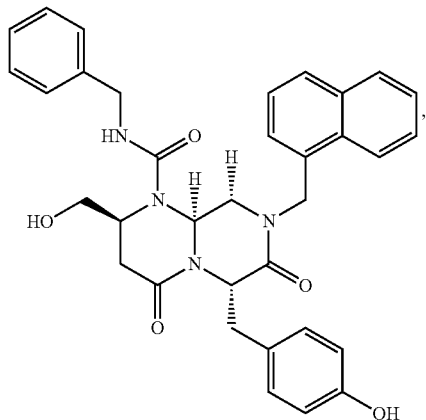
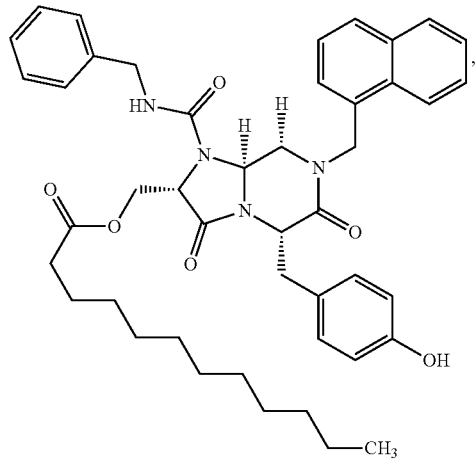
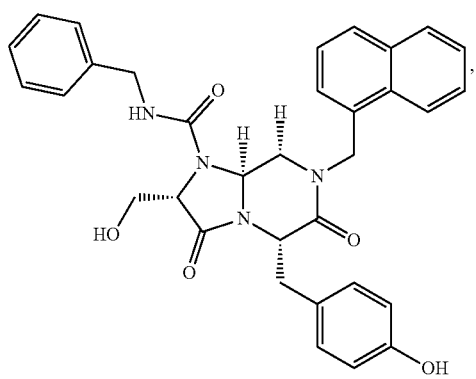
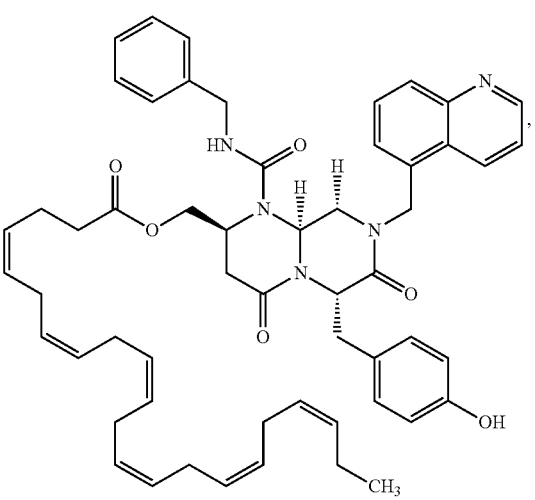
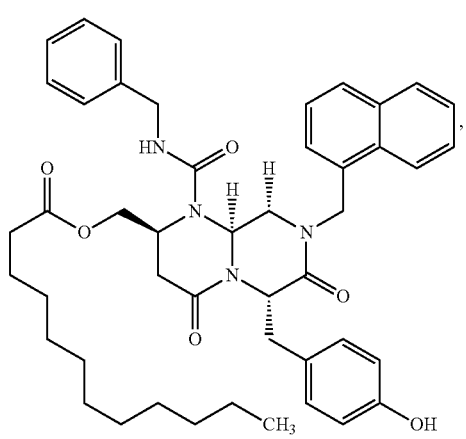
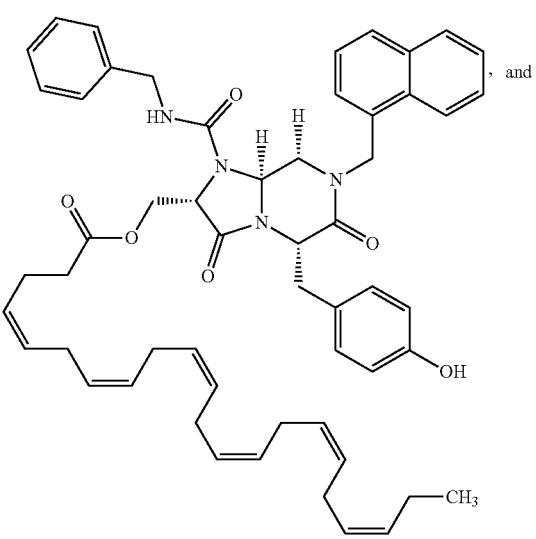, and -continued

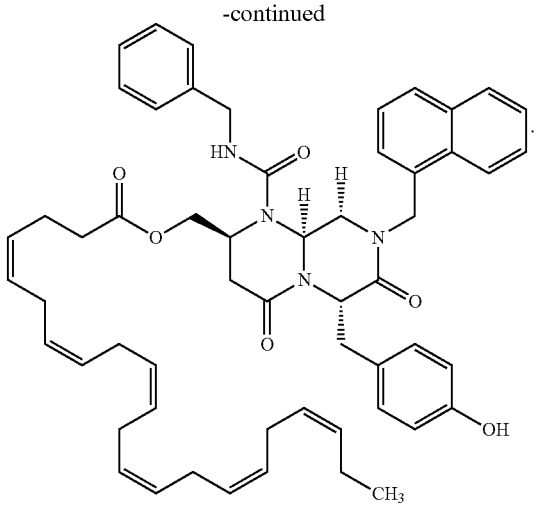

6. A composition comprising at least one compound of any one of clauses 1 to 5.

7. The composition of clause 6, wherein the composition is a pharmaceutical and/or a cosmeceutical composition comprising a pharmaceutically acceptable or cosmeceutically acceptable excipient, respectively.

8. A method for cosmetically treating a skin condition, comprising topically administering to a mammalian subject in need thereof, a cosmeceutically effective amount of a compound of any one of clauses 1-5.

9. The method of clause 8, wherein the skin condition is mediated by CREB binding protein (CBP)/β-catenin signaling, and wherein the amount is sufficient to inhibit the CBP/β-catenin signaling.

10. The cosmetic method of clause 8 or 9, wherein the skin condition comprises one or more aging skin conditions selected from wrinkles, hyperpigmentation, redness, rosacea, dryness, cracking, loss of vibrance, loss of elasticity, thinning, scarring, acne, sun or U.V. damage, hair loss, loss of hair coloration, reduced eyebrow or eyelash growth, reduced cuticle growth, and/or reduced nail growth.

11. The method of any one of clauses 8-10, wherein, for the compound, Y is not hydrogen.

12. The method of clause 11, wherein Y is —C(O)R, and wherein R is selected from:

![structure with (CH2)m chain]

wherein m is 1 to 10.

13. Use of a compound of any one of clauses 1 to 5 for manufacturing of a cosmeceutical for cosmetic treatment of a skin condition.

14. The use of clause 13, wherein the skin condition comprises one or more of wrinkles, hyperpigmentation, redness, rosacea, dryness, cracking, loss of vibrance, loss of elasticity, thinning, scarring, acne, sun or U.V. damage, hair loss, loss of hair coloration, reduced eyebrow or eyelash growth, reduced cuticle growth, reduced nail growth.

15. The use of clause 13 or 14, wherein, for the compound, Y is not hydrogen.

16. Use of a compound of any one of clauses 1 to 5 for manufacturing of a medicament for treatment of a skin disease or disorder.

17. The use of clause 16, wherein the skin disease or disorder is mediated, at least in part, by CREB binding protein (CBP)/β-catenin signaling, and wherein the treatment is sufficient to inhibit, at least in part, the CBP/β-catenin signaling.

18. The use of clause 16 or 17, wherein the skin disease or disorder comprises one or more of atopic dermatitis, psoriasis, acne, fibrosis, wounding, scarring, post-laser surgical scarring, burns, sun or U.V. damage, actinic keratosis, diabetic ulceration, and/or alopecia.

19. The use of any one of clauses 16-19, wherein, for the compound, Y is hydrogen.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
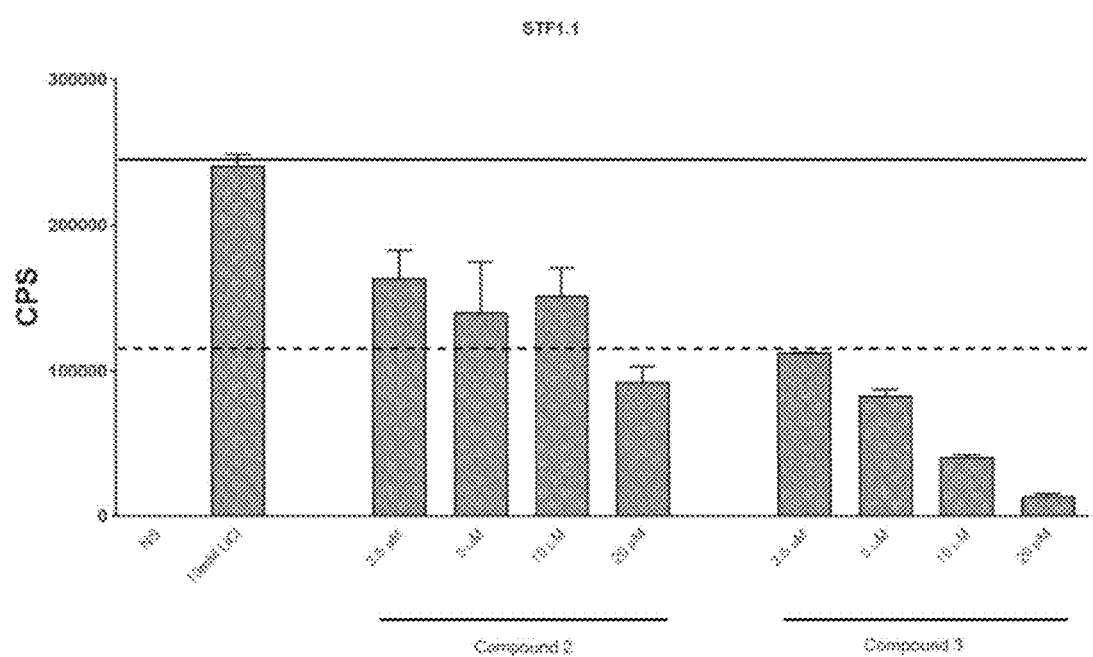
FIG. 1 shows, according to non-limiting aspects of the present invention, results of a SuperTOPFLASH™ cell-based luciferase assay (Wnt-driven luciferase activity in stably transfected cell line, Hek293, STF1.1), comparing the CBP/βcatenin inhibition activities of two exemplary compounds of the present invention (compound 2 and compound 3) at 2.5, 5, 10 and 20 µM concentrations. Compound 3 was shown to be potent with an $IC_{50}$ value of 2.5 µM.

Provided are compounds of formula (I):

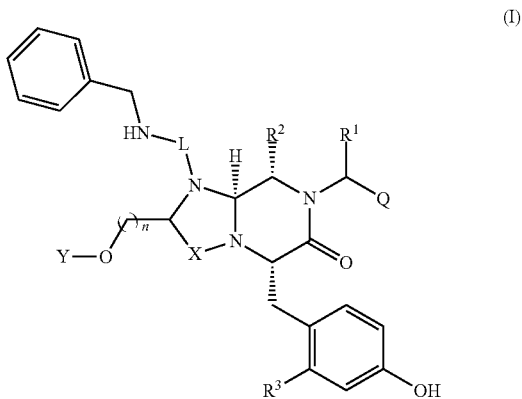

and solvates (e.g., hydrates), metabolites, isotopically-labeled derivatives, and any pharmaceutically and/or cosmeceutically acceptable salts thereof, wherein:

R¹ and R² are independently selected from: hydrogen or —CH₃;

R³ is hydrogen or deuterium;

Q is a phenyl group; a substituted phenyl group having one or more substituents wherein the one or more substituents are independently selected from one or more of amino, amidino, guanidino, hydrazino, amidazonyl, $C_{1-4}$ alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl, and hydroxyl groups; a benzyl group; a substituted benzyl group with one or more substituents where the one or more substituents are independently selected from one or more of amino, amidino, guanidino, hydrazino, amidazonyl, $C_{1-4}$alkylamino, $C_{1-4}$dialkylamino, halogen, perfluoro $C_{1-4}$alkyl, $C_{1-3}$alkoxy, nitro, carboxy, cyano, sulfuryl, and hydroxyl group; or a bicyclic aryl group having 8 to 11 ring members, which may have 1 to 3 heteroatoms independently selected from nitrogen, oxygen or sulfur;

L is —C(O)—, or —SO₂—;

X is —C(O)—, or —CH₂C(O)—;

n is 1 or 2;

Y is hydrogen, or —C(O)R, wherein R is $C_1$-$C_{30}$alkyl, $C_1$-$C_{30}$alkylene, or $C_1$-$C_{30}$ alkylene.

The compounds may be of formula (Ia):

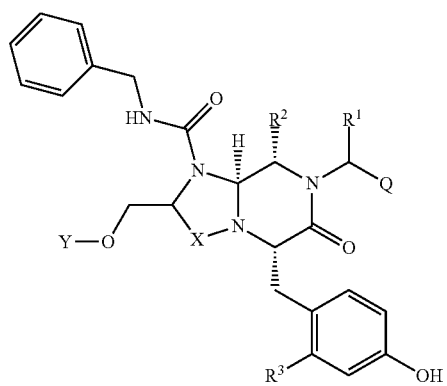

(Ia)

and solvates (e.g., hydrates), metabolites, isotopically-labeled derivatives, and any salts including pharmaceutically and/or cosmeceutically acceptable salts thereof, wherein:

R¹, R², R³, X, and Y are as defined above for formula (1); and wherein

Q is selected from naphthyl, quinolinyl, isoquinolinyl, phthalazine, quinazoline, cinnoline, or naphthyridine.

Preferably, the provided compounds are of formula (Ib) and formula (Ic):

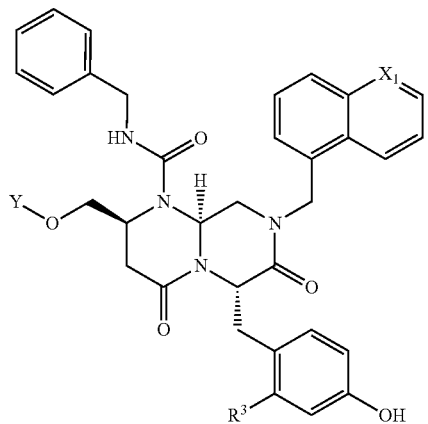

(Ib)

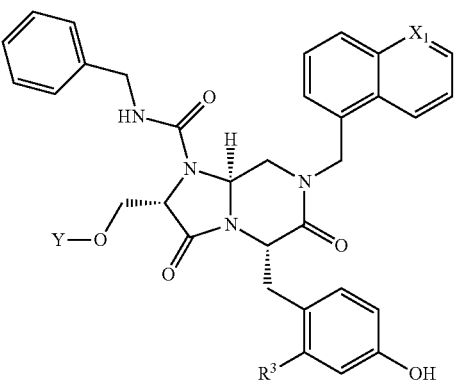

(Ic)

and solvates (e.g., hydrates), metabolites, isotopically-labeled derivatives, and any salts including pharmaceutically and/or cosmeceutically acceptable salts thereof, wherein:

X₁ is N, or —CH,

R³ is hydrogen or deuterium;

Y is hydrogen, or —C(O)R, wherein R is $C_1$-$C_{30}$alkyl, $C_1$-$C_{30}$alkenyl, or $C_1$-$C_{30}$ alkylene.

In the compounds of formula (I), (Ia), (Ib), and (Ic), where Y is not hydrogen, R is preferably selected from:

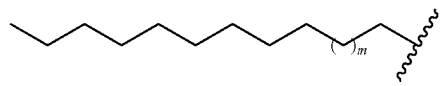

wherein m is 1 to 10, or

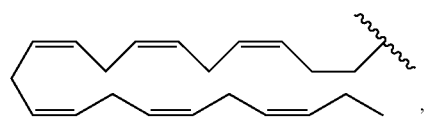

or
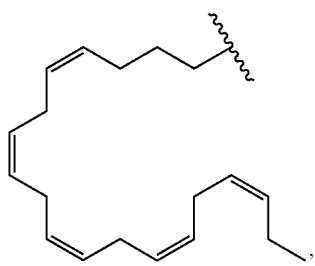
or
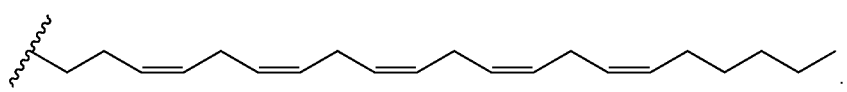
Particular preferred compounds are:
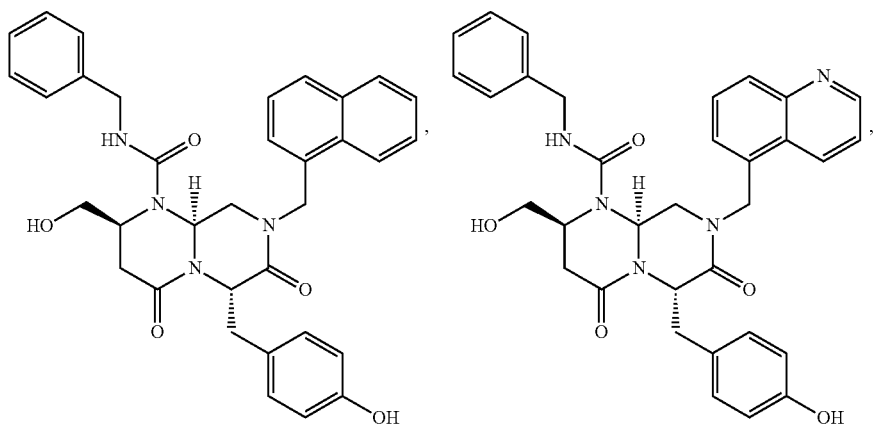
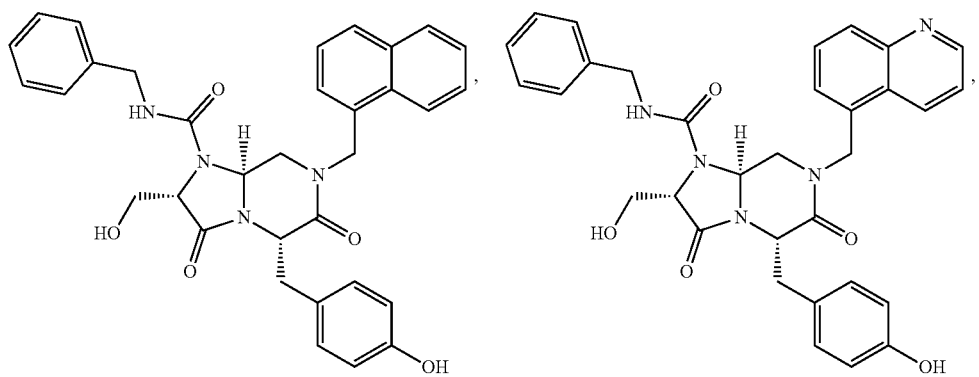

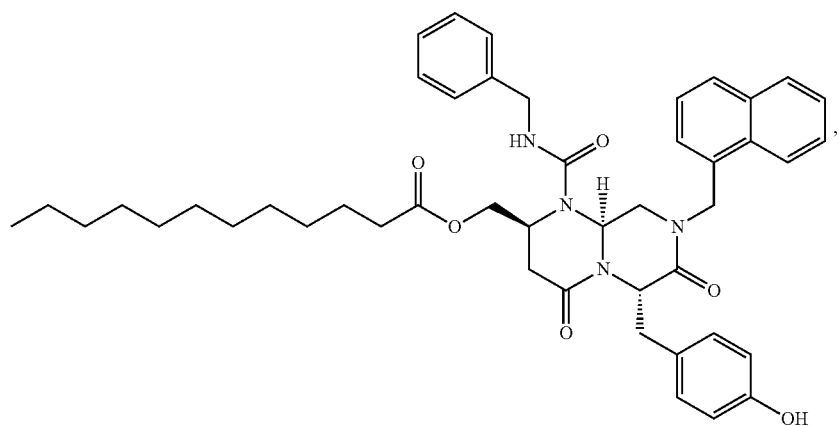
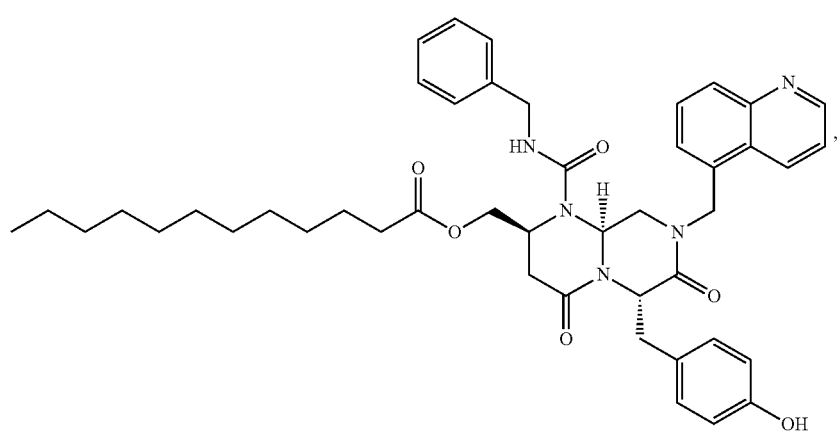
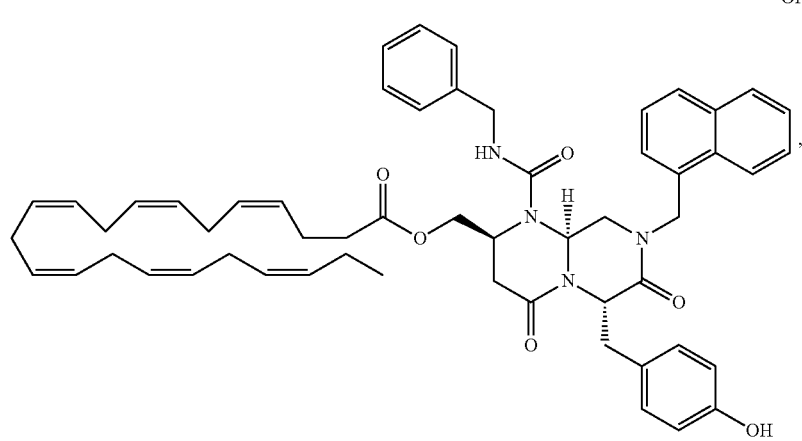
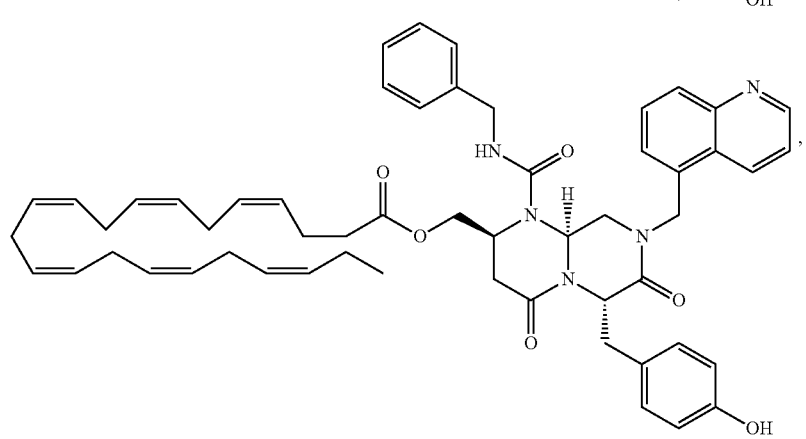

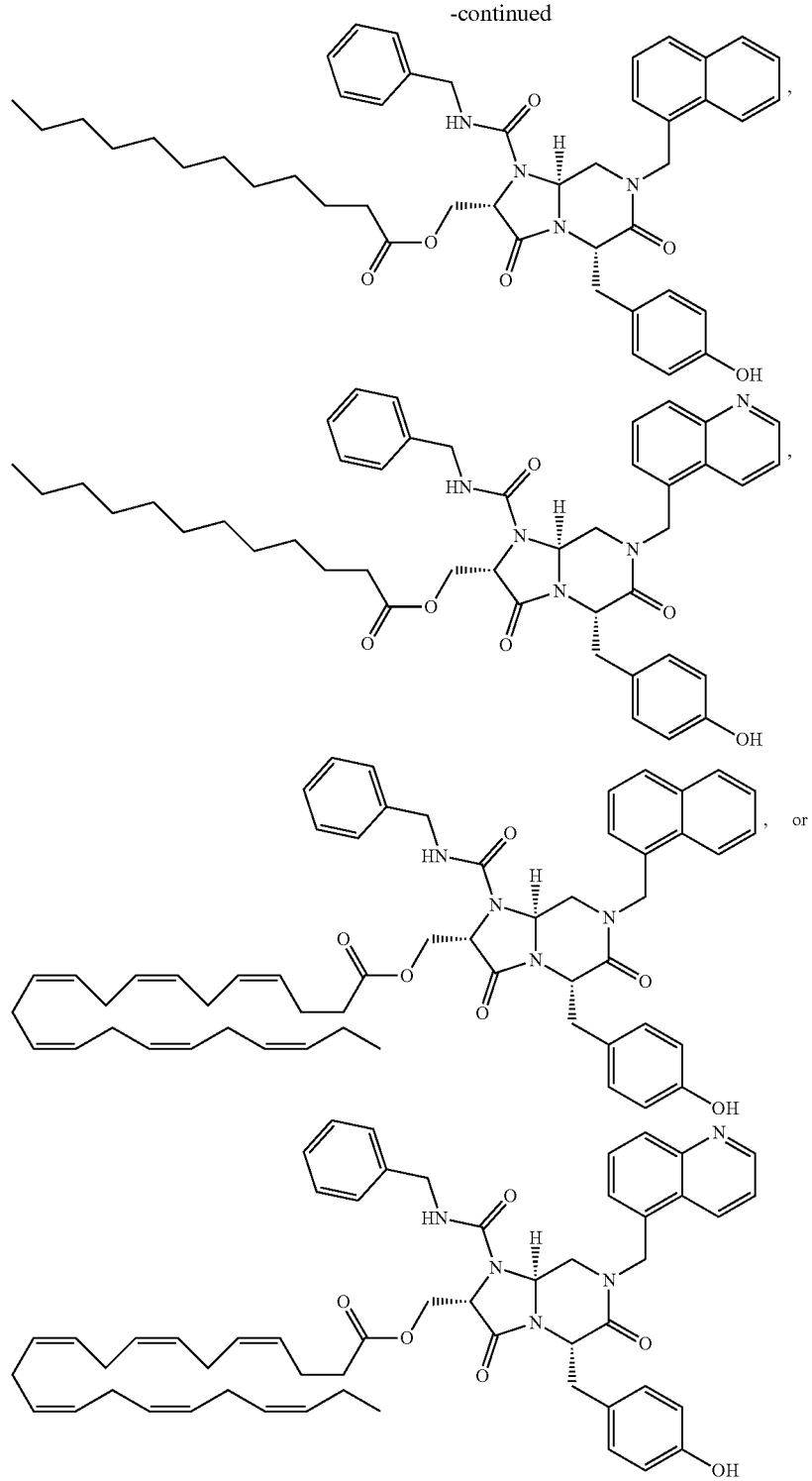

and compositions and pharmaceutical and/or cosmetical compositions comprising the compounds disclosed herein, and optionally comprising a pharmaceutically or cosmeceutically acceptable excipient or carrier.

According to aspects of the present invention, compounds of formula (I), formula (Ia), formula (Ib) and formula (Ic) are potent modulators of the Wnt/δ-catenin pathway that inhibit CBP/β-catenin mediated signaling.

Provided, therefore, are pharmaceutical and/or cosmeceutical compounds, and compositions comprising these compounds, and uses of these compounds and compositions for the treatment of any aberrant CBP/β-catenin signaling-mediated skin related diseases, conditions, or disorders (e.g., dermatitis, psoriasis, alopecia, etc), or aging related skin conditions selected from wrinkles, hyperpigmentation, redness, rosacea, dryness, cracking, loss of vibrance, loss of elasticity, thinning, scarring, acne, sun damage, hair loss, loss of hair coloration, reduced cuticle growth, reduced nail growth, reduced eyelash or eyebrow growth.

The compounds of formula (I), formula (Ia), formula (Ib) and formula (Ic) of the present invention may contain chiral centers and therefore may exist in different enantiomeric and diastereomeric forms. This invention relates to all optical isomers and all stereoisomers of compounds having the structures as defined above, both as racemic mixtures and as individual enantiomers and diastereoisomers of such compounds, and mixtures thereof, and to all pharmaceutical compositions and cosmeceutical compositions and methods of treatment defined below that contain or employ them, respectively. In some embodiments, the preferred compounds are the (S)-enantiomer. In other embodiments, the preferred compounds are the (R)-enantiomer. Alternatively, for the disclosed methods, the compounds are racemic mixtures.

As the compounds of the present invention may possess at least two asymmetric centers, they are capable of occurring in various stereoisomeric forms or configurations. Hence, the compounds can exist in separated (+)- and (−)-optically active forms, as well as mixtures thereof. Compounds and methods of the present invention encompass all such forms within the scope of the disclosure. Individual isomers can be obtained by known methods, such as optical resolution, optically selective reaction, or chromatographic separation in the preparation of the final product or its intermediate.

Aspects of the present invention also include isotopically labeled compounds, which are identical to those recited in the present invention, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds according to formula (I), formula (Ia), formula (Ib), and formula (Ic) described herein or pharmaceutically acceptable salts, tautomers, isomers, prodrugs, or solvates of said compounds or of said prodrugs which contain the aforementioned isotopes and/or other isotopes of other atoms are encompassed within the scope of this invention. Certain isotopically-labeled compounds of the present invention, for example those into which radioactive isotopes such as $^{3}H$ and $^{14}C$ are incorporated, are useful in drug and/or substrate tissue distribution assays. In addition, it is known that the deuterium atom ($^{2}H$) is a non-radioactive isotope of the hydrogen atom. Such compounds may increase resistance to metabolism, and thus may be useful in the disclosed methods for increasing the half-life of the compounds of the present invention or pharmaceutically acceptable salts, isomers, prodrugs, or solvates thereof, when administered to a mammal (see: e.g., Foster, A. B., Trends Pharmacol. Sci. 1984; 5(12): 524-527). Isotopically labeled compounds of this invention can generally be prepared by carrying out the procedures disclosed in the Examples of Preparations below, by substituting a readily available isotopically labeled reagent for a non-isotopically labeled reagent.

Also provided are pharmaceutical compositions and pharmaceutical and/or cosmeceutical dermatologically acceptable topical formulations comprising one or more of the disclosed compounds in an amount sufficient when topically administered to a warm-blooded mammalian subject having a skin condition, or disease or disorder mediated by aberrant CBP/β-catenin signaling, to specifically inhibit the CBP/β-catenin mediated signaling within the subject. The amount of the topical administered compound preferably comprises a cosmeceutically and/or therapeutically effective amount, and in such cases the pharmaceutical and/or cosmeceutical dermatologically acceptable compositions and formulations may comprise a cosmeceutically and/or therapeutically effective amount of the compound having a structure disclosed herein or a pharmaceutically and/or cosmeceutically dermatologically acceptable salt thereof and a pharmaceutically and/or cosmeceutically dermatologically acceptable carrier, diluent, or excipient therefor. All of these formulations are encompassed within the scope of the present invention. In preferred embodiments, the amount of the topically administered compound in the pharmaceutically and/or cosmeceutically dermatologically acceptable formulations is in the range of 0.5% (w/w) to 0.05% (w/w).

Definitions

The term "CBP protein" refers to the protein that is also known as CREB-binding protein, where CREB is an abbreviation for "cAMP-response element binding." This protein is well known in the art (see, e.g., Takemaru, K. I., et al., J. Cell Biol. 2000; 149:249-54; U.S. Pat. No. 6,063,583).

The phrase "Wnt pathway" refers to a signaling cascade that may be initiated by the binding of Wnt proteins (secreted glycoproteins) to frizzled seven-transmembrane-spanning receptors. This pathway is known and characterized in the art and is the subject of numerous articles and reviews (see: e.g., Huelsken, J., et al., J. Cell Sci. 2002; 115:3977-8; Wodarz, A., et al., Annu. Rev. Cell Dev. Biol. 1998; 14:59-88; Morin, P. J., Bioessays 1999; 21:1021-30; Moon, R. T., et al., Science 2002; 296:1644-46; Oving, I. M., et al., Eur. J. Clin. Invest. 2002; 32:448-57; Sakanaka, C., et al., Recent Prog. Horm. Res. 2000; 55:225-36). Classical Wnt signaling (termed canonical Wnt signaling or Wnt/beta-catenin signaling) has as its hallmark a soluble pool of cytoplasmic beta-catenin, associated with the degradation complex that consists of the core proteins Axin, APC, GSK3 (glycogen synthase kinase 3), and CK1-alpha (casein kinase 1- alpha). In the absence of Wnt ligand, β-catenin is phosphorylated within this complex thereby targeting it for ubiquitination and subsequent destruction by the proteasomal machinery (Kohn, A. D., et al., Cell Calcium 2005; 38:439-446). Activation of the Wnt pathway triggers a series of events that disrupts the APC/Axin/GSK3 complex that is required for the targeted destruction of β-catenin, and thereby promotes the stabilization and accumulation of β-catenin in the cytoplasm. This build-up in the cytoplasm coincides with the translocation of β-catenin into the nucleus through a mechanism that is still not entirely defined. In the nucleus, β-catenin, in the classical definition of the Wnt signaling cascade, forms a complex with members of the TCF/LEF family of transcription factors. To generate a transcriptionally active complex, β-catenin recruits the transcriptional coactivators, cAMP response element-binding protein (CREB)-Binding Protein (CBP) or its closely related homolog, p 300 (E1A-Binding Protein, 300-KD) as well as other components of the basal transcription machinery, leading to the expression of a host of downstream target genes (Logan, V. Y., et al., Ann Rev Cell Dev Biol 2004; 20:781-810; Angers, S., et al., Ann Rev Cell Dev Biol 2009; 10:468-477).

"Alkyl" means a linear or branched, saturated, aliphatic radical having a chain of carbon atoms.

"Alkenyl" means a linear or branched, carbon chain that contains at least one carbon-carbon double bond.

"Alkylene," unless indicated otherwise, means a linear or branched, saturated or un-saturated, aliphatic, polyvalent carbon chain.

"Protected derivatives" means derivatives of compound in which a reactive site or sites are blocked with protecting groups. A comprehensive list of suitable protecting groups can be found in T. W. Greene, *Protecting Groups in Organic Synthesis*, 3rd edition, John Wiley & Sons, Inc. 1999.

"Isomers" mean any compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are non-superimposable mirror images are termed "enantiomers" or sometimes "optical isomers." A carbon atom bonded to four non-identical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry," 4th edition, March, Jerry, John Wiley & Sons, New York, 1992).

"Animal" includes humans, non-human mammals (e.g., mice, rats, dogs, cats, rabbits, cattle, horses, sheep, goats, swine, deer, apes, monkeys, and the like) and non-mammals (e.g., birds, and the like).

"Mammal" includes human and non-human mammals, preferably warm-blooded mammals.

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Cosmeceutically acceptable" means that which is useful in preparing a cosmeceutical composition that is generally safe, non-toxic and neither biologically nor otherwise undesirable and includes that which is acceptable for veterinary use as well as human cosmeceutical use.

"Pharmaceutically acceptable salt" or "salt" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like. Pharmaceutically acceptable salts also include base addition salts, which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Amount effective to treat" or "therapeutically effective amount" means that amount which, when administered to an animal for treating a disease, is sufficient to effect such treatment for the disease.

A "cosmeceutically effective amount" is amount which, when administered (e.g., transdermal, topical) is sufficient to affect cosmetic treatment of a cosmetic condition (e.g., wrinkles, hyperpigmentation, redness, rosacea, dryness, cracking, loss of vibrance, loss of elasticity, thinning, scarring, acne, sun damage, hair loss, loss of hair coloration, reduced cuticle growth, reduced nail growth).

"Amount effective to prevent" means that amount which, when administered to an animal for preventing a disease, condition or disorder, is sufficient to effect such prophylaxis for the disease, condition or disorder.

"Treatment" or "treat" means any administration of a compound of the present invention and includes: (i) preventing a disease, condition or disorder from occurring in an animal which may be predisposed to the disease, condition or disorder but does not yet experience or display the pathology or symptomatology of the disease, condition or disorder; (ii) inhibiting the disease, condition or disorder in an animal that is experiencing or displaying the pathology or symptomatology of the disease, condition or disorder (i.e., arresting further development of the pathology and/or symptomatology); or (iii) ameliorating the disease, condition or disorder in an animal that is experiencing or displaying the pathology or symptomatology of the disease, condition or disorder (i.e., reversing the pathology and/or symptomatology).

"Topical delivery" refers to dermal delivery (e.g., delivery into the skin).

Uses and Composition and Formulations of Exemplary Compounds of the Present Invention:

The exemplary inventive compounds disclosed herein provide novel antagonists with unexpected potency to inhibit CBP/β-catenin signaling. Based on animal toxicity studies and human clinical studies, and as recognized in the art, known specific CBP/β-catenin antagonists (e.g., ICG-001) are extremely safe at effective dose levels. Since many skin and hair conditions may require long-term administration, a large safety margin is favorable to physicians and patients alike. Thus, according to aspects of the invention, since the disclosed exemplary inventive compounds are specific CBP/β-catenin antagonists, they are of value in the treatment of any aberrant CBP/β-catenin signaling mediated skin related conditions, or diseases or disorders, including aging related skin conditions.

The present invention also provides prodrugs using one or more compounds of formula (I), formula (Ia), formula (Ib), and/or formula (Ic). The term "prodrug" as used herein refers to compounds that are rapidly transformed in vivo to yield the active drug having structure as defined herein, for example, during or after absorption by enzymatic cleavage in blood or tissues. A thorough discussion is provided in Higuchi et al., Pro-drugs as Novel Delivery Systems, Vol. 14 of the A.C.S. Symposium Series, and in Roche (ed.),"Bioreversible Carriers in Drug Design," American Pharmaceutical Association and Pergamon Press, (1987), both of which are hereby incorporated by reference. In the present invention, the use, for example, of an alkyl or fatty acid ester-containing prodrug approach is to enhance topical delivery via increasing the lipophilicity of the parent drug, and such change is designed to facilitate absorption or permeation across the stratum corneum into the viable epidermis and beyond, and importantly, to be readily cleaved to release the parent drug when exposed to skin microenvironments and esterases.

Provided, therefore, are inventive compounds that are specific CBP/β-catenin antagonists having substantial utility for use in treating skin related diseases or disorders or conditions, and for cosmetic applications (e.g., in aging subjects). Therapeutically relevant exemplary skin related diseases, conditions or disorders include those that occur in skin structure, including but not limited to wounds, acne, sun damage, certain skin diseases or conditions for which there is currently no cure (e.g., latent viral infection of epidermal or mucosal tissues), ulcers (e.g., diabetic), burns, atopic dermatitis, psoriasis. Cosmeceutically relevant exemplary conditions include, but are not limited to, effects of aging, and including wrinkles, hyperpigmentation, dryness, redness, cracking, rosacea, firmness, elasticity, thickness, appearance, etc. Cosmetic usage may include improvement and preventive applications for both skin, nail and hair structure. In addition, the compounds of the present invention can be used to promote skin stem cell differentiation, and display a broad range of beneficial effects, such as accelerating skin healing, promoting skin maintenance, and delaying skin aging. Aspects of the invention, therefore, provide therapeutic and/or cosmetic methods for treating skin related diseases, conditions, or disorders, comprising administering (e.g., topically or otherwise) a therapeutically and/or cosmeceutically effective amount of an inventive compound to a subject in need thereof, in such amounts and for such time as is necessary to achieve the desired result. Adjunctive and combination therapy embodiments are also encompassed and provided.

Additional aspects of the present invention provide pharmaceutical and/or cosmeceutical compositions, comprising at least one of the inventive compounds disclosed herein and/or pharmaceutical and/or cosmeceutically acceptable salts thereof, and optionally comprise a pharmaceutically and/or cosmeceutically acceptable carrier, diluent, or excipient. The pharmaceutical and/or cosmeceutical compositions of the present invention are formulated to be compatible with an intended route of administration (e.g., forms of local or systemic administration). Preferably, administration of a compound of the present invention comprises topical administration. As used herein, a pharmaceutically and/or cosmeceutically acceptable carrier or diluent refers to a carrier or diluent that does not cause significant irritation to an organism and does not abrogate the biological activity and properties of the administered compound. The pharmaceutical and/or cosmeceutical compositions may further comprise inert diluents such as additional solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Pharmaceutical and/or cosmeceutical compositions of the present invention may include, in addition to a least one inventive compound, one or more of: water caprylic/capric triglyceride, glycerin, dimethicone, cetearyl alcohol, arachidyl alcohol, arachidyl glucoside, cetearyl glucoside. sclerotium gum, tetrasodium glutamate diacetate, behenyl alcohol, xanthan gum, sodium hydroxide, citric acid, hexylene glycol, ethylhexylglycerin, caprylyl glycol, phenoxyethanol, etc.

Techniques for formulation and administration of pharmaceutical compositions can be found in Remington's Pharmaceutical Sciences, 18th Ed., Mack Publishing Co, Easton, Pa., 1990; and Modern Pharmaceutics, Marcel Dekker, Inc. 3rd Ed. (G. S. Banker & C. T. Rhodes, Eds.). The pharmaceutical compositions are formulated to contain suitable pharmaceutically acceptable carriers, and optionally can comprise excipients and auxiliaries that facilitate processing of the active compounds into preparations that can be used pharmaceutically. The mode of administration generally determines the nature of the carrier. The pharmaceutical and/or cosmeceutical compositions of the present invention can be manufactured using any conventional method, e.g., mixing, dissolving, granulating, dragee-making, levigating, emulsifying, encapsulating, entrapping, melt-spinning, spray-drying, or lyophilizing processes.

The compounds and pharmaceutical and/or cosmeceutical compositions of the present invention can be formulated and employed in combination therapies or treatments, that is, the compounds and pharmaceutical and/or cosmeceutical compositions of the present invention can be formulated with or administrated concurrently with, prior to, or subsequent to, one or more other desired therapeutics or medical procedures (e.g., such as simultaneously or adjunctively treating the subject with an anti-skin aging agent).

An optimal pharmaceutical and/or cosmeceutical formulation can be determined by one of skill in the art depending on the route of administration and the desired dosage. The present invention encompasses pharmaceutically or cosmeceutically dermatological acceptable formulations (e.g., topical) of inventive compounds. The term "pharmaceutically or cosmeceutically dermatological acceptable topical formulations," as used herein, refers to any formulation which is pharmaceutically or cosmeceutically dermatological acceptable to deliver a therapeutically and/or cosmeceutically effective amount of a compound of the present invention in skin layers, to exert a local effect. In certain embodiments, the amount of the topical administered inventive compound in the pharmaceutically and/or dermatologically acceptable formulations is in the range of 0.5% (w/w) to 0.05% (w/w). In certain other embodiments, the topical formulation comprises a carrier system. As used herein, "pharmaceutically acceptable carrier," "cosmeceutically acceptable carrier" and "carrier" generally refer to components that are chemically inert to the therapeutic agents, and that have no detrimental side effects or toxicity under the conditions of use, i.e., non-toxic, inert solid, semi-solid or liquid filler, diluent, encapsulating material or formulation auxiliary of any type (e.g., including creams and lotions, emulsions, jellies, depot formulations). Pharmaceutically and/or cosmeceutically dermatological effective carriers include, but are not limited to, solvents (e.g., water), creams, lotions, ointments, oils, plasters, liposomes, powders, emulsions, microemulsions, and buffered solutions (e.g., buffered saline) or any other carrier known in the art for topically administering therapeutics and/or consmeceutical agents. The pharmaceutically and/or cosmeceutically acceptable carriers may include polymers and polymer matrices, nanoparticles, microbubbles, and the like. In certain other embodiments, the topical formulations of the invention may comprise excipients. Any pharmaceutically and/or cosmeceutically dermatological acceptable excipient known in the art may be used to prepare the inventive pharmaceutically and/or cosmeceutically dermatological acceptable topical formulations. Examples of excipients include, but are not limited to, preservatives, antioxidants, moisturizers, emollients, buffered agents, solubilizing agents, other penetration agents, skin protectants, surfactants, propellants. In certain embodiments, the composition formulation may also comprise at least one additional agent selected from the group consisting of carriers, adjuvants, emulsifying agents, suspending agents, sweeteners, flavorings, perfumes, and binding agents.

Administration:

In general, most suitable means of administration of a compound or composition for a particular subject will depend on the nature and severity of the disease, disorder or condition being treated or the nature of the therapy and/or cosmetic treatment being used, as well as the nature of the therapeutic and/or cosmetic composition or additional therapeutic and/or cosmetic agent. Examples of routes of administration include intradermal, subcutaneous, transdermal (topical), and transmucosal administration. The pharmaceutical and/or cosmeceutical composition of the present invention is formulated to be compatible with its intended route of administration. Preferably, topical administration is used.

Accordingly, the final dosage regimen will be determined by good medical practice, considering various factors that modify the action of drugs, e.g., the agent's specific activity, the identity and severity of the disease, disorder or condition state, the responsiveness of the patient, the age, condition, body weight, sex, and diet of the patient, and the severity (e.g., of any infection). Additional factors that can be considered include time and frequency of administration, drug combinations, reaction sensitivities, and tolerance/response to therapy. Further refinement of the dosage appropriate for treatment involving any of the formulations mentioned herein is done routinely by the skilled practitioner without undue experimentation, especially in light of the dosage information and assays used.

Yet further aspects provide kits comprising an inventive compound or composition, a container, and optionally a package insert or label indicating a treatment. In one embodiment, the container may be a vial, jar, ampoule, preloaded syringe, or an intravenous bag. The term "package insert" refers to instructions customarily included in commercial packages of therapeutic and/or cosmetic products that contain information about the indications, usage, dosage, administration, contraindications and/or warnings concerning the use of such therapeutic and/or cosmetic products. Suitable containers include, e.g., bottles, vials, syringes, blister pack, etc. The container may be formed from a variety of materials such as glass or plastic.

Working Examples

An illustration of the preparation of exemplary compounds of the present invention is provided in the representative Examples and Schemes below, wherein specific non-limiting examples of compounds are intended to illustrate particular embodiments of the present invention, and are not intended to limit the scope of the specification or the claims in any way. The compounds of the present invention may be prepared by the synthetic sequence shown in the non-limiting Examples and Schemes below. A skilled artisan will appreciate that other routes of synthesis may be employed as well. In particular, other routes of synthesis may in fact be applied to certain aspects of the present invention. For example, (R)-3-(((9H-fluoren-9-yl)methoxy)carbonylamino)-4-(tert-butyldimethylsilyloxy)butanoic acid can be prepared according to Step 1-2 of Example 3, and used for the synthesis of compound 2. The skilled artisan is referred to general textbooks, such as March's Advanced Organic Chemistry (Michael B. Smith & Jerry March, Wiley-Interscience, 2000), The Practice of Medicinal Chemistry (Camille G. Wermuth, Academia Press, 2003) and Protective Groups in Organic Synthesis (Theodora W. Greene & Peter G. M. Wuts; John Wiley & Sons Inc, 1999), all incorporated by reference herein for their respective teachings.

Example 1

Reagents, Synthetic Methods, and Biological Characterization Assays Used

Unless otherwise noted, all reagents, starting materials and solvents were obtained from commercial suppliers and used without further purification. Concentration or evaporation refers to evaporation under vacuum using a Buchi rotatory evaporator. Reaction products were purified by silica-gel chromatography with the solvent system indicated, or by HPLC purification using a C18 reverse phase semi-preparative HPLC column with solvent A (0.1% of TFA in water) and solvent B (0.1% of TFA in $CH_3CN$) as eluents. All final products have at least 95% purity as determined by analytical HPLC analysis with UV detection at 210 nm and/or 254 nm. Reported yields are isolated yields.

Analytical HPLC analysis was performed on an Agilent 1100 HPLC with a Phenomenex Luna C18 (2) column (3 micron, 150×4.6 mm id) at a flow rate of 0.6 mL/min, eluting with a binary solvent system A and B using a 35%-70% B in 20 min and then 70%-95% B in 5 min (gradient elution 1), or 70%-95% B in 25 min and then 95%-100% B in 3 min (gradient elution 2) (A: Milli-Q water with 0.1% TFA; B: $CH_3CN$ with 0.1% TFA). NMR spectra were recorded on a Bruker AV-300 300 MHz NMR instrument using DMSO-$d_6$ or $CDCl_3$ with TMS as an internal standard. Mass spectra data was obtained with Bruker Esquire Liquid Chromatography-Ion Trap Mass Spectrometer.

The following abbreviations are used in the synthetic examples: aq (aqueous), h (hour), min (minutes), sat'd (saturated), THF (tetrahydrofuran), rt (room temperature), $Et_3N$ (triethylamine), NaCl (sodium chloride), $MgSO_4$ (magnesium sulfate), $CDCl_3$ (deuterated chloroform), $H_2O$ (water), HCl (hydrochloric acid), MeOH (methanol), NaOH (sodium hydroxide), TFA (trifluoroacetic acid), $Na_2CO_3$ (sodium carbonate), $CH_2Cl_2$ (methylene chloride), EtOAC (ethyl acetate), DMF (dimethylformamide), EtOH (ethanol), DMSO (dimethyl sulfoxide), DMSO-$d_6$ (dimethyl sulfoxide-$d_6$), $NaHCO_3$ (sodium bicarbonate), HPLC (high performance liquid chromatography), ESI-MS or MS (ESI) (electrospray ionization-mass spectrometry), NMR (nuclear magnetic resonance), DIEA (diisopropylethylamine), brine (saturated aqueous NaCl solution), HATU (1-[Bis(dimethylamino)methylene]-1H-1,2,3-triazolo[4,5-b]pyridinium-3-oxide hexafluorophosphate), and other similar standard abbreviations are used herein.

Biological characterization of exemplary compounds of the present invention was performed in at least the following assays:

Assay of Wnt/driven TCF/LEF reporter (Luc) activity in a stably transfected cell line. The Wnt/driven TCF/LEF reporter (Luc) activity in a stably transfected cell line assay was performed at BPS Bioscience (San Diego, Calif. 92121, USA). In brief, TCF/LEF reporter (Luc)-HEK293 cells are harvested from culture in growth medium and seeded at a density of about 35,000 cells per well into a white clear-bottom 96-well microplate in 80 μL of assay medium. 20 μL of 50 mM LiCl solution in assay medium are added to each well (final concentration 10 mM), and cells are incubated at 37° C. in a $CO_2$ incubator for 16 hours. 10 μL of threefold serial dilution of mouse Wnt3a in assay medium are added to each stimulated well. The plate is incubated at 37° C. in a $CO_2$ incubator for 6 hours. 100 μL of ONE-Step™ Luciferase Assay buffer per well are added and the plate is shaken for 30 min prior to measuring luminescence using a luminometer.

SuperTOPFLASH Cell-based Luciferase Assay. Hek-293, STF1.1 cells are maintained in DMEM, 10% FBS, Pen-Strep supplemented with 200 μg/mL G418. On the day prior to assay, cells are split into a white, opaque 96-well plate at 10,000 cells per well in 50 μL of complete medium without G418 (for screening of Wnt-signaling inhibitors, G418 can be left out during screening process). After allowing the cells to stabilize and attach overnight, 40 μL of complete medium (without G418) containing 2.5× final concentration of compound or DMSO control is added to the cells and allowed to incubate for 1 hour at 37° C., 5% $CO_2$ prior to adding 10 μL of a 100 mM LiCl solution prepared in complete medium (without G418). After 24 hours, 100 μL of BrightGlo™ (Promega, Cat. #: G7573) is added to each well and the plate is shaken for 5 minutes prior to reading on the Perkin-Elmer EnVision™ Plate Reader. For example, on the day prior to assay: cells are split into a white opaque 96-well plate at 10,000 cells per well in 50 μL of complete growth medium; the plate is incubated overnight at 37° C., 5% $CO_2$ and the cells allowed to attach; the next day inhibitors to be tested are prepared in complete growth medium at 2.5× the desired final concentration (all conditions are done in duplicates), and 40 μL of the medium containing the 2.5× concentration of compound is added to each well (include 2 wells for stimulation control, 2 wells for DMSO control; once all inhibitors and controls are added, incubate the plate for 1 hour at 37° C., 5% $CO_2$ (while plate is incubating, prepare fresh 100 mM LiCl in complete growth medium); after 1 hour, the plate is removed from the incubator and 10 μL of the medium containing 100 mM LiCl are added to each well (except for the two wells of the unstimulated control, to which 50 microliters of just complete medium is added); the plate is incubated for 24 hours at 37° C., 5% $CO_2$; after 24 hours, 100 microliters of BrightGlo™ (Promega, Cat. #: G7573) is added to each well, the plate is shaken for 5 minutes to ensure complete lysis, and the plate is then read on a Perkin-Elmer EnVision™ 96-well plate reader.

Example 2

Synthesis of (S)-2-amino-3-(4-tert-butoxyphenyl)-N-(2,2-diethoxyethyl)-N-(naphthalen-1-ylmethyl) propanamide (1)

Compound 1 was prepared according to the procedures disclosed in U.S. Pat. No. 7,671,054, as shown in Scheme 1, starting from 1-naphthaldehyde. The title compound 1 as a colorless oil. MS (ESI): m/z 493.3 (M+H)⁺; analytical HPLC: 15.3 min.

Scheme 1

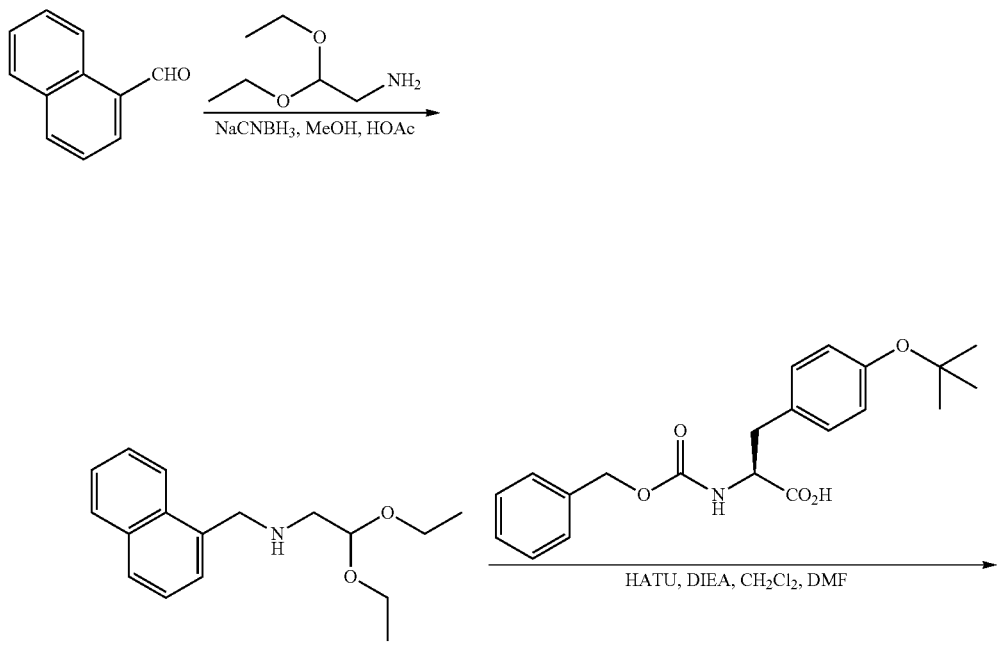

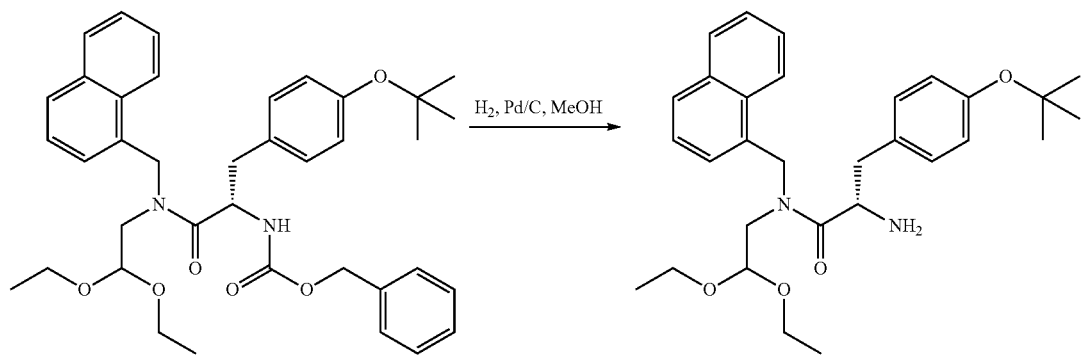
Example 3
Synthesis of (2R,6S,9aS)-N-benzyl-6-(4-hydroxybenzyl)-2-(hydroxymethyl)-8-(naphthalen-1-ylmethyl)-4,7dioxohexahydro2H-pyrazino[1,2-a]pyrimidine-1(6H)-carboxamide (2)
Compound 2 was prepared according to the procedures set forth in steps 1-6 of Scheme 2 below:
Scheme 2
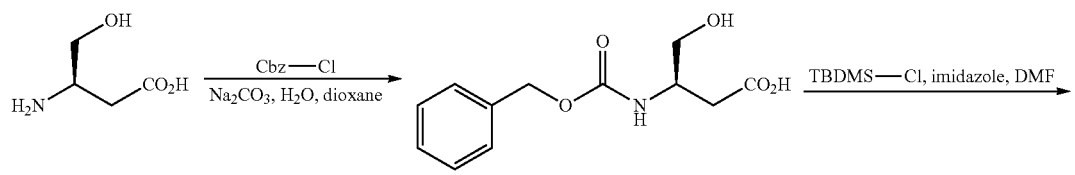
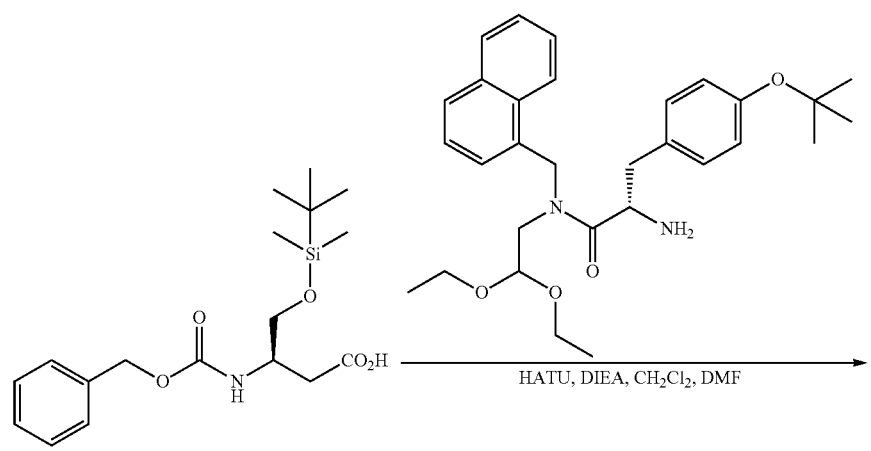

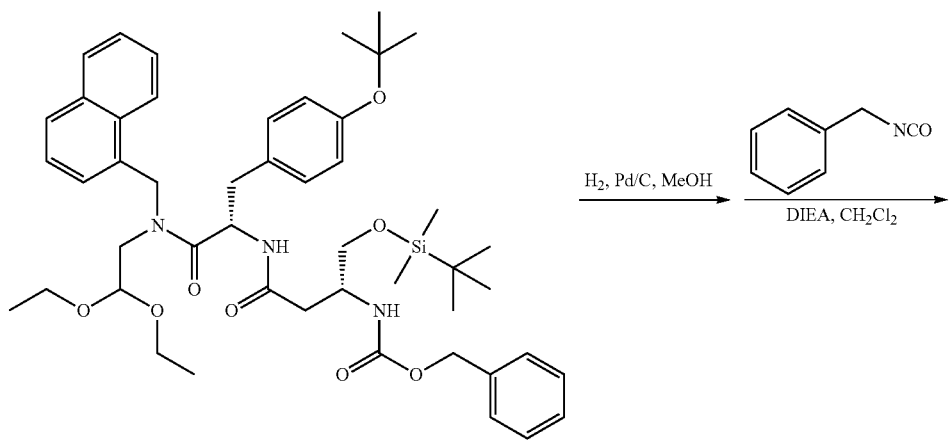

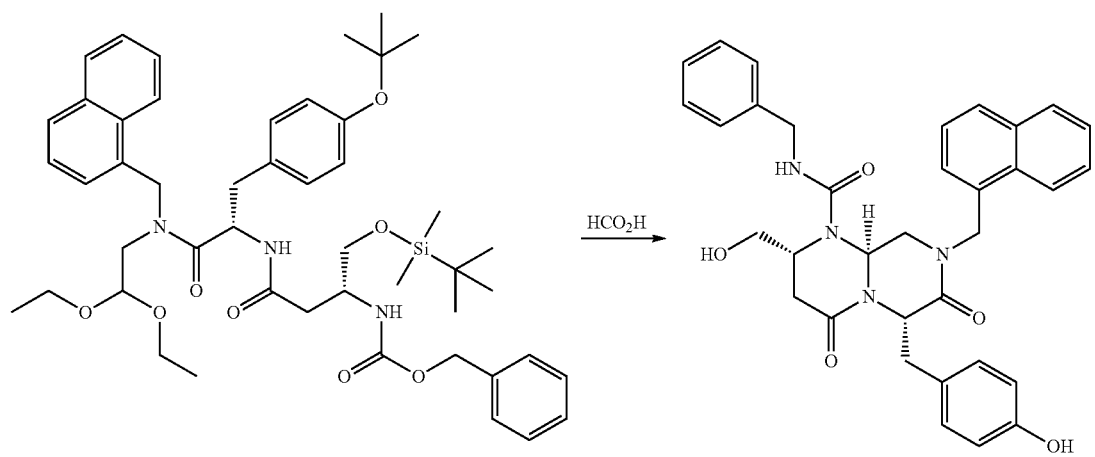

Step 1-2: (R)-3-(benzyloxycarbonylamino)-4-(tert-butyldimethylsilyloxy)butanoic acid The compound was prepared according to the procedures reported (Andres J. M., et. al., Eur. J. Org. Chem. 2003; 17: 3387-3397; Luppi, G., et al., Synlett. 2003; 6:797-800), using (R)-3-amino-4-hydroxybutanoic acid as the starting material.

Step 3: benzyl ((6R,10S)-10-(4-(tert-butoxy)benzyl)-14-ethoxy-2,2,3,3-tetramethyl-12-(naphthalen-1-ylmethyl)-8,11-dioxo-4,15-dioxa-9,12-diaza-3-silaheptadecan-6-yl)carbamate To a solution of (S)-2-amino-3-(4-tert-butoxyphenyl)-N-(2,2-diethoxyethyl)-N-(naphthalen-1-ylmethyl)propanamide (268 mg, 0.544 mmol) and (R)-3 -(benzyloxycarbonylamino)-4-(tert-butyldimethylsilyloxy)butanoic acid (200 mg, 0.544 mmol) in $CH_2Cl_2$ (4.1 mL) and DMF (0.41 mL) at 0° C. was added HATU (207 mg, 0.544 mmol) and DIEA (0.174 mL, 1.09 mmol). The reaction mixture was stirred at 0° C. for 0.5 hour and at room temperature overnight under argon, and concentrated under reduced pressure, and then taken into ethyl acetate (25 mL) and water (25 mL). The organic layer was washed with brine (15 mL), dried ($Na_2SO_4$), and evaporated. The crude material was purified by silica-gel chromatography using 25% and 35% EtOAc/Hexane to give the desired product (0.246 g, 54%) as a colorless oil. MS (ESI): m/z 842.4 $(M+H)^{+}$ Step 4: (R)-3-amino-N-((S)-3-(4-tert-butoxyphenyl)-1-((2,2-diethoxyethyl)(naphthalen-1-ylmethyl)amino)-1-oxopropan-2-yl)-4-(tert-butyldimethylsilyloxy)butanamide To a solution of benzyl (6R,10S)-10-(4-tert-butoxybenzyl)-14-ethoxy-2,2,3,3-tetramethyl-12-(naphthalen-1-ylmethyl)-8,11-dioxo-4,15-dioxa-9,12-diaza-3-silaheptadecan-6-ylcarbamate (246 mg, 0.29 mmol) in $CH_3OH$ (6 mL) was added Pd/C (26 mg). The reaction mixture was stirred under $H_2$ atmosphere at room temperature overnight. Filtration via Celite and evaporation afforded the desired product (0.20 g, 95%) as a pale-yellow oil, which was used in the next step without further purification. Analytical HPLC: 23.7 min.

Step 5: (R)-3-(3-benzylureido)-N-((S)-3-(4-tert-butoxyphenyl)-1-((2,2-diethoxyethyl)(naphthalen-1-ylmethyl)amino)-1-oxopropan-2-yl)-4-((tert-butyldimethylsilyl)oxy)butanamide To a solution of (R)-3-amino-N-((S-3(4-tert-butoxyphenyl)-1-((2,2-diethoxyethyl) (naphthalen-1-ylmethyl)amino)-1-oxopropan-2-yl)-4-(tert-butyldimethylsilyloxy)butanamide (196 mg, 0.23 mmol) in CH$_2$Cl$_2$ (2.7 mL) was added benzyl isocyanate (54 μL, 0.39 mmol). The reaction mixture was stirred at room temperature overnight, and concentrated under reduced pressure. The resulting residues were purified on silica gel chromatography with 50% EtOAc/hexane to afford the title compound (0.16 g, 83%) as a white residue. MS (ESI): m/z 842.0 (M+H)$^+$.

Step 6: (2R, 6S,9aS)-N-benzyl-6-(4-hydroxybenzyl)-2-(hydroxymethyl)-8 -(naphthalen-1-ylmethyl)-4,7dioxohexahydro-2H-pyrazino[1,2-a]pyrimidine-1 (6H)-carboxamide A solution of crude of (R)-3-(3-benzylureido)-N-((S)-3-(4-tert-butoxyphenyl)-1-((2,2-diethoxyethyl)(naphthalen-1-ylmethyl)amino)-1-oxopropan-2-yl)-4-(tert-butyldimethylsilyloxy)butanamide (0.156 g) in formic acid (8 mL) was stirred at room temperature over 20 hours and evaporated to dryness. The resulting residues were treated with conc. NH$_4$OH in CH$_3$OH at room temperature over 2 hours and evaporated to dryness to give a crude product (128 mg). The crude material (33 mg) was purified by preparative HPLC to give the desired product (13 mg) as a white solid. MS (ESI): m/z 579.2 (M+H)$^+$; analytical HPLC: 13.4 min (98% pure).

Example 4

Synthesis of (2S,6S,9aS)-N-benzyl-6-(4-hydroxybenzyl)-2-(hydroxymethyl)-8-(naphthalen-1-ylmethyl)-4,7-dioxohexahydro-2H-pyrazino[1,2-a]pyrimidine-1(6H)-carboxamide (3)

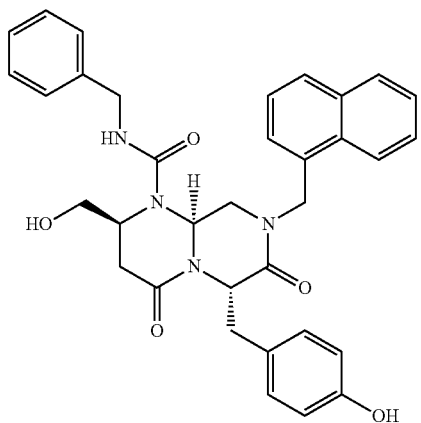 [SMILES: O=C1[C@H](Cc2ccc(O)cc2)N2C(=O)C[C@@H](CO)N(C(=O)NCc3ccccc3)[C@H]2CN1Cc1cccc2ccccc12]

Compound 3 was prepared according to the procedures described in Example 3, using (S)-3-amino-4-hydroxybutanoic acid as the starting material. MS (ESI): m/z 579.2 (M+H)$^+$; analytical HPLC: 12.0 min (99% pure).

Example 5

Synthesis of (2S,5S,8aS)-N-benzyl-5-(4-hydroxybenzyl)-2-(hydroxymethyl)-7-(naphthalen-1-ylmethyl)-3,6-dioxohexahydroimidazo[1,2-a]pyrazine-1 (5H)-carboxamide (4)

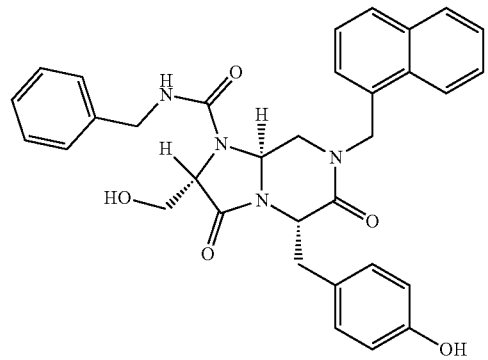 [SMILES: O=C1[C@H](Cc2ccc(O)cc2)N2C(=O)[C@H](CO)N(C(=O)NCc3ccccc3)[C@H]2CN1Cc1cccc2ccccc12]

Compound 4 was prepared according to the procedures described in Example 3, using (R)-2-amino-3-hydroxypropanoic acid as the starting material. MS (ESI): m/z 565.3 (M+H)$^+$; analytical HPLC: 14.0 min (98% pure).

The compound (2R,5S,8aS)-N-benzyl-5-(4-hydroxybenzyl)-2-(hydroxymethyl)-7 -(naphthalen-1-ylmethyl)-3,6-dioxohexahydroimidazo[1,2-a]pyrazine-1(5H)-carboxamide was synthesized, according to the procedures described in Example 3, using (S)-2-amino-3-hydroxypropanoic acid as the starting material. The desired product was obtained with a low yield.

Example 6

Synthesis (2R,5S,8aS)-N-benzyl-5-(4-hydroxybenzyl)-2-(2-hydroxyethyl)-7-(naphthalen-1-ylmethyl)-3,6-dioxohexahydroimidazo[1,2-a]pyrazine-1(5H)-carboxamide (5)

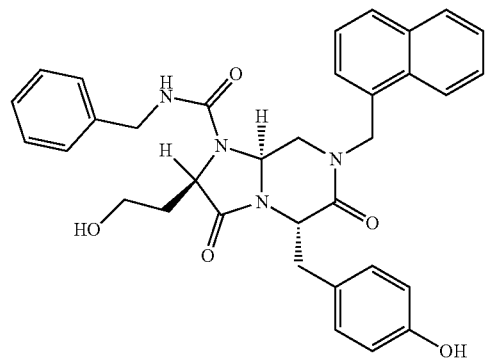 [SMILES: O=C1[C@H](Cc2ccc(O)cc2)N2C(=O)[C@@H](CCO)N(C(=O)NCc3ccccc3)[C@H]2CN1Cc1cccc2ccccc12]

Compound 5 is prepared according to the procedures described in Example 3, using (R)-2-amino-4-hydroxybutanoic acid as the starting material. MS (ESI): m/z 579.2 (M+H)$^+$; analytical HPLC: 13.6 min (99% pure).

Example 7
Synthesis of Compounds defined in Formula (Ib) and Formula (Ic), wherein Y is
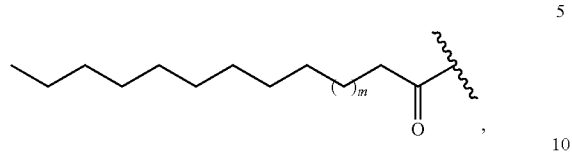
wherein m is 1 to 10
Exemplary compound 6, (2S,6S,9aS)-1-(benzylcarbamoyl)-6-(4-hydroxybenzyl)-8-(naphthalen-1-ylmethyl)-4,7-dioxooctahydro-2H-pyrazino[1,2-a]pyrimidin-2-yl)methyl dodecanoate, was prepared according to the procedures set forth in steps 1-3 of Scheme 3 below:
Scheme 3
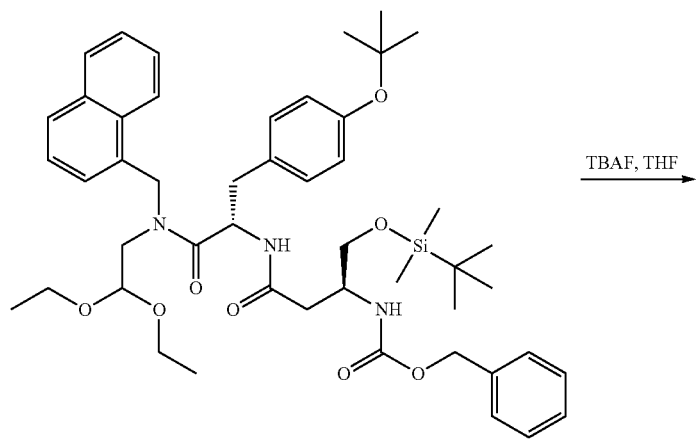
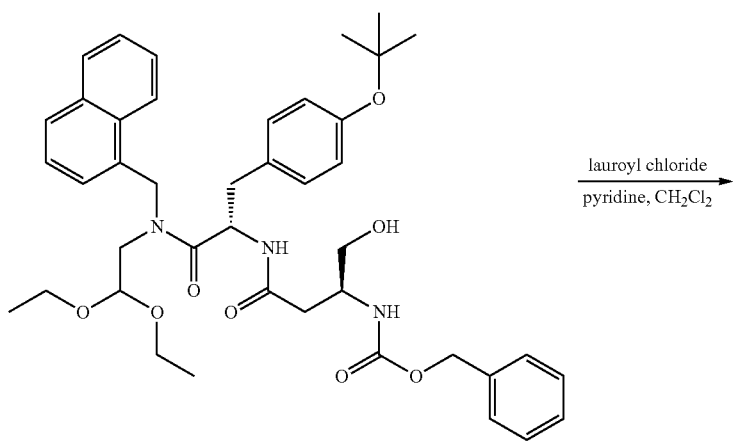

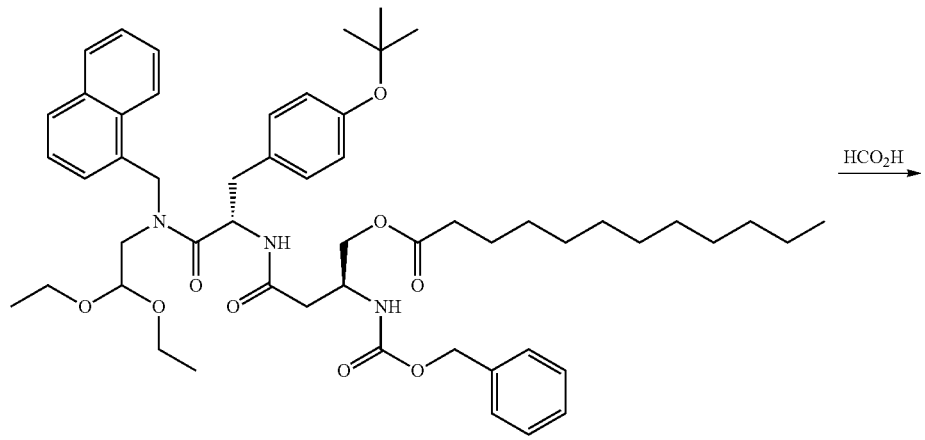

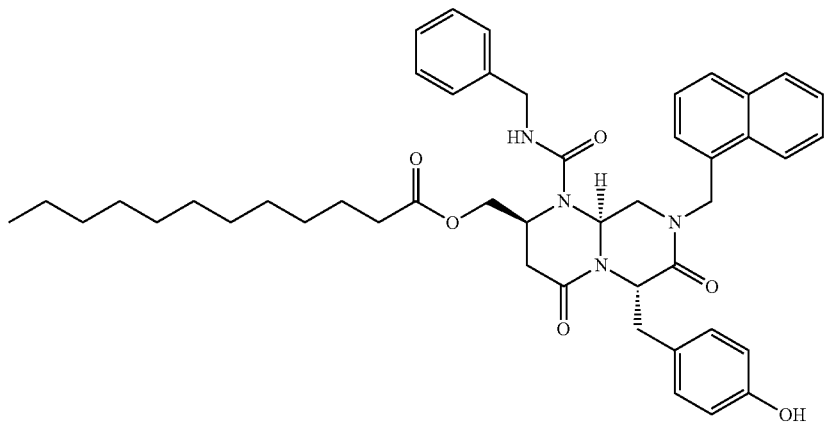

Step 1: (S)-3-(3-benzylureido)-N-((S)-3-(4-tert-butoxyphenyl)-1-((2,2-diethoxyethyl) (naphthalen-1-ylmethyl)amino)-1-oxopropan-2-yl)-4-hydroxybutanamide To a solution of (S)-3-(3-benzylureido)-N-((S)-3-(4-tert-butoxyphenyl)-1-((2,2-diethoxyethyl)(naphthalen-1-ylmethyl)amino)-1-oxopropan-2-yl)-4-(tert-butyldimethylsilyloxy)butanamide (3.5 g, 4.16 mmol) in THF (62 mL) at 0° C. was added TBAF (1 N, 8.3 mL) dropwise. The reaction mixture was stirred at room temperature overnight under argon, and evaporated to dryness. The crude material was purified by silica-gel chromatography using 5% $CH_3OH$/ $CH_2Cl_2$ to give the desired product (3.3 g, 100%) as a white foam. MS (ESI): m/z 727.8 (M+H)$^+$.

Step 2: (S)-2-(3-benzylureido)-4-(((S)-3-(4-tert-butoxy)phenyl)-1-((2,2-diethoxyethyl)(naphthalen-1-ylmethyl)amino)-1-oxopropan-2-yl)amino)-4-oxobutyl dodecanoate To a solution of (S)-3-(3-benzylureido)-N-((S)-3-(4-tert-butoxyphenyl)-1-((2,2-diethoxyethyl)(naphthalen-1-ylmethyl)amino)-1-oxopropan-2-yl)-4-hydroxybutanamide (1.98 g, 2.72 mmol) in dry $CH_2Cl_2$ (48 mL) at 0° C. was added pyridine (0.44 mL, 5.4 mmol) and lauroyl chloride (0.82 mL, 3.54 mmol). The reaction mixture was stirred under argon at 0° C. for 1 hour and at room temperature overnight. After addition of water (4.0 mL) at 0° C., the reaction mixture was evaporated to dryness. The crude material was purified by silica-gel chromatography using 5% $CH_3OH/CH_2Cl_2$ to give the desired product (2.3 g, 93%) as a white solid. MS (ESI): m/z 910.4 (M+H)$^+$.

Step 3: ((2S,6S,9aS)-1-(benzylcarbamoyl)-6-(4-hydroxybenzyl)-8-(naphthalen-1-ylmethyl)-4,7-dioxooctahydro-2H-pyrazino[1,2-a]pyrimidin-2-yl) methyl dodecanoate A solution of (S)-2(3-benzoylureido)-4-((S)-3-(4-tert-butoxyphenyl)-1-((2,2-diethoxyethyl)(naphthalen-1-ylmethyl) amino)-1-oxopropan-2-ylamino)-4-oxobutyl dodecanoate (2.3 g, 2.5 mmol) in formic acid (80 mL) was stirred at room temperature over 24 hours and evaporated to dryness. The resulting residues were purified by silica-gel chromatography using 25% and 50% EtOAc/$CH_2Cl_2$ to give the desired product (1.28 g, 67%) as a white foam. MS (ESI): m/z 761.6 (M+H)$^+$; analytical HPLC: 16.9 min (98% pure; gradient elution 2).

Example 8

Synthesis of Compounds defined in Formula (Ib) and Formula (Ic), wherein Y is

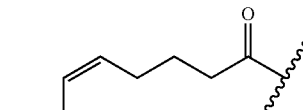, 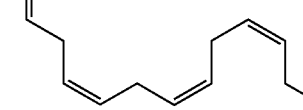, or

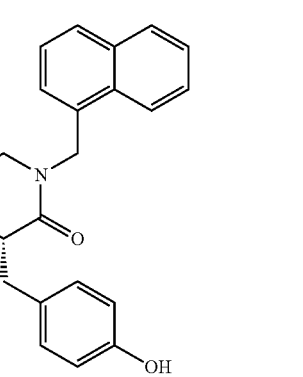, or

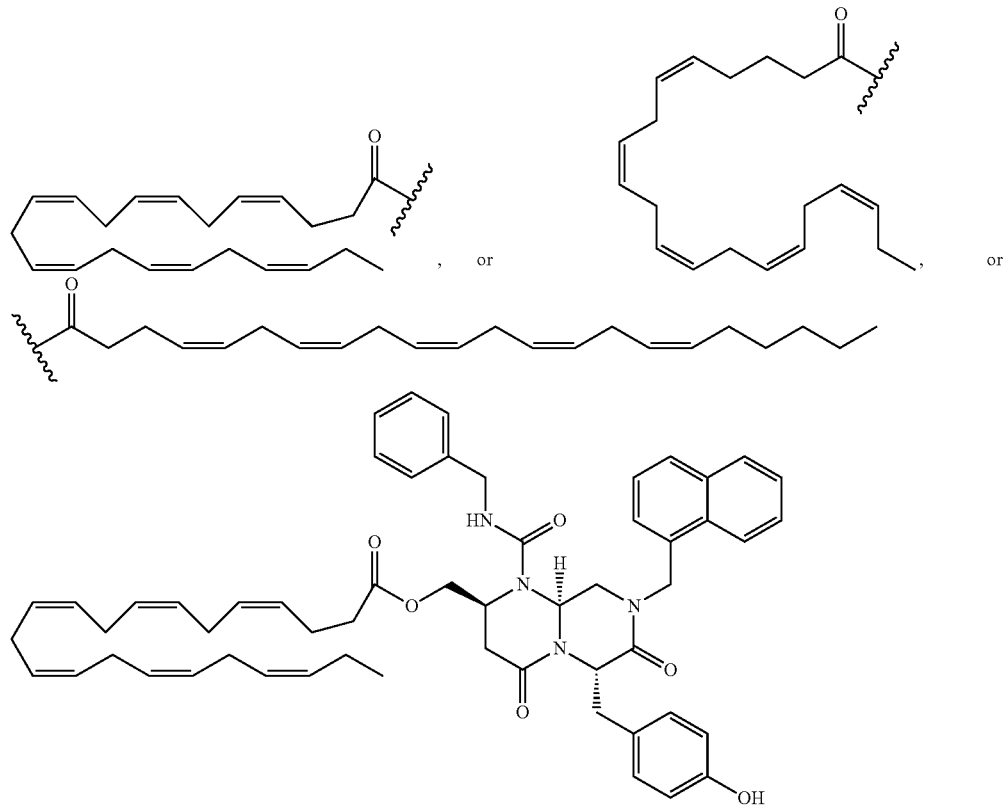

Exemplary compound 7, ((2S,6S,9aS)-1-(benzylcarbamoyl)-6-(4-hydroxybenzyl)-8-(naphthalen-1-ylmethyl)-4,7-dioxooctahydro-2H-pyrazino[1,2-a]pyrimidin-2-yl)methyl (4Z,7Z,10Z,13Z,16Z,19Z)-docosa-4,7,10,13,16,19-hexaenoate, was prepared according to the procedures as described in Example 7, using docosahexaenoic acid chloride instead, as a pale-yellow foam. MS (ESI): m/z 889.7 (M+H)$^+$; analytical HPLC: 22.1 min (96% pure; gradient elution 2).

Example 9

Biological Characterization of Exemplary Compounds of Formula (Ib) and Formula (Ic), wherein Y is Hydrogen, in the Wnt/driven TCF/LEF Reporter (Luc) Activity in HEK293 Cell Line Assay Exemplary compounds, wherein Y is hydrogen, of the present invention were tested for Wnt/driven TCF/LEF reporter (Luc) activity in HEK293 cell line assay. The IC$_{50}$ values of the compounds against TCF/LEF reporter activity are summarized in Table 1. As demonstrated in Table 1, the unexpected inhibitory activity or potency of the exemplary compounds of formula (Ib) and formula (Ic), wherein Y is hydrogen, is attributed to the optimal selection of the chirality at 2 positions of the bicyclic rings, and n equal 1 is required for optimal inhibition. In both bicyclo[5,6] and bicyclo[6,6] systems, the S-configuration of —CH$_2$OH is needed to most potently inhibit the TCF/LEF reporter activity. The positive control compound for this assay is IWR-1-endo, which is known in the art as a non-CBP/β-catenin Wnt antagonist, which stabilizes Axin-dependent β-catenin destruction (Chen, B., et al., Nat. Chem. Biol. 2009; 5(2): 100-107).

TABLE 1

IC$_{50}$ value of compounds against TCF/LEF reporter activity

| Compound | IC$_{50}$ (μM) |
|---|---|
| 2 | >25 |
| 3 | 16 |
| 4 | 11.2 |
| 5 | >25 |
| IWR-1-endo (positive control) | 0.2 |

Example 10

Biological Characterization of Exemplary Compounds 2 and 3 in the SuperTOPFLASH Cell-Based Luciferase Assay FIG. 1 shows, according to non-limiting aspects of the present invention, results of a SuperTOPFLASH cell-based luciferase assay (Wnt-driven luciferase Activity in Stably Transfected Cell Line, Hek293, STF1.1), comparing the CBP/β-Catenin inhibition activities of two exemplary compounds, compound 2 and compound 3, of the present invention in concentrations at 2.5, 5, 10 and 20 μM. The inventive compound 3 has IC$_{50}$ value of 2.5 μM, further demonstrating that the S-configuration of —CH$_2$OH at the 2-position of bicyclic rings is required for optimal inhibition activity.

Example 11

Figure 2A:
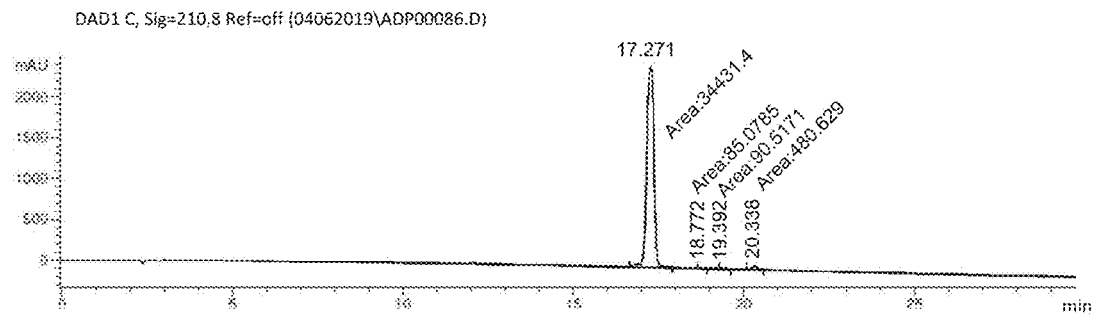
FIG. 2A, FIG. 2B, and FIG. 2C show, according to non-limiting aspects of the present invention, the stability of an exemplary fatty acid ester prodrug of the present invention (compound 6; coded NP-002) by analytical HPLC analysis. Compound 6 was shown to be stable at room temperature both as a solid form and in organic solvents.
Figure 2B:
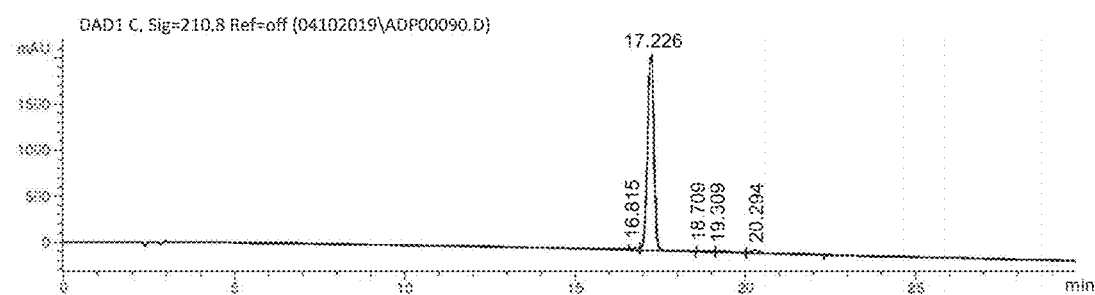
Figure 2C:
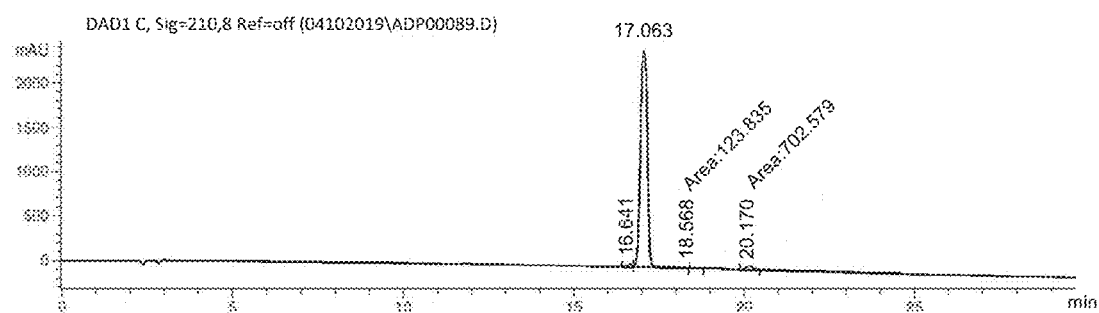

Stability of an Exemplary Prodrug of the Present Invention (Compound 6; Coded NP-002) by Analytical HPLC Analysis FIG. 2 shows, according to non-limiting aspects of the present invention, the stability of an exemplary prodrug of the present invention (compound 6; coded NP-002) by analytical HPLC analysis. As is readily apparent, compound 6 is stable at room temperature both in a solid form and in organic solvents (e.g., CH$_3$CN, and CH$_3$OH). No degradation product of compound 6 after 4 days at room temperature was detected based on analytical HPLC analysis.

Example 12

Cosmetic Evaluation of an Exemplary Prodrug of the Present Invention (Compound 6; Coded NP-002) on Human Skin For cosmetic evaluation, compound 6 (0.15% wt./wt.) formulated in an aqueous based vehicle was topically applied twice daily (0.25 g formulation per application) during an 8-week testing period according to the following daytime/nighttime regimen.

During the study, subjects used no other skin care regimen. Prior to application of the test formulation, subjects washed their faces with Purpose cleanser, rinsed and then dry patted their faces. For each daytime and each nighttime application, 0.25 g of the test formulation (2 pumps from an applicator) was then applied to the entire face, around the eyes and onto the neck. Photographs (without any face and eye make-up), and self-assessment was performed before and after the 8-week period.

Figure 3A:
FIG. 3A and FIG. 3B show, according to non-limiting aspects of the present invention, the significant dermatological effect of an exemplary fatty acid ester prodrug of the present invention (compound 6; coded NP-002) on human skin (treatment period: 8 weeks). Skin improvement (e.g., reducing the extent and appearance of wrinkles) was visible after 8-weeks treatment using compound 6 in a topical dermatological formulation.
Figure 3B:

FIG. 3 shows, according to non-limiting aspects of the present invention, a significant cosmetic dermatological effect of exemplary compound 6 on human skin (treatment period: 8 weeks). As is readily apparent, improvement of skin appearance (e.g., reducing the appearance of wrinkles and redness) is achieved after the 8-week treatment using compound 6 in a topical dermatological formulation.

The invention and the manner and process of making and using it, are now described in such full, clear, concise, and exact terms as to enable any person skilled in the art to which it pertains, to make and use the same.

It will be appreciated that, although specific embodiments of the invention have been described herein for the purposes of illustration, various modifications may be made without departing from the spirit and scope of the invention. Accordingly, the invention is not limited except by the appended claims.

All of the above U.S. patents, U.S. patent application publications, U.S. patent applications, foreign patents, foreign patent applications and non-patent publications referred to in this specification, are incorporated herein by reference.

What is claimed is:

1. A compound of formula (I):

(I)

or a cosmeceutically acceptable or pharmaceutically acceptable salt thereof,
wherein:
L is —C(O)— or —S(O)$_2$—;
X is —C(O)— or —CH$_2$C(O)—;
Y is H or C(O)R;
R is C$_{1-30}$ alkyl or C$_{2-30}$ alkenyl;
R$^1$ is H or CH$_3$;
R$^2$ is H or CH$_3$;
R$^3$ is H or D;
Q is benzyl, phenyl, or an 8- to 11-membered aryl;
wherein the 8- to 11-membered aryl is bicyclic;
wherein the 8- to 11-membered aryl optionally contains 1, 2, or 3 heteroatoms independently selected from the group consisting of nitrogen, oxygen, and sulfur;
wherein the benzyl is optionally substituted with one or more substituents independently selected from the group consisting of halogen, CN, NO$_2$, C$_{1-4}$ perfluoroalkyl, C(NH)NH$_2$, C(O)OH, NH$_2$, NHC$_{1-4}$ alkyl, N(C$_{1-4}$ alkyl)$_2$, NHC(NH)NH$_2$, OH, and OC$_{1-4}$ alkyl; and
wherein the phenyl is optionally substituted with one or more substituents independently selected from the group consisting of halogen, CN, NO$_2$, C$_{1-4}$ alkyl, C$_{1-4}$ perfluoroalkyl, C(NH)NH$_2$, C(O)OH, NH$_2$, NHC$_{1-4}$ alkyl, N(C$_{1-4}$ alkyl)$_2$, NHC(NH)NH$_2$, OH, and OC$_{1-4}$ alkyl; and
n is 1 or 2.

2. The compound of claim 1, wherein the compound is of formula (Ia):

(Ia)

or a cosmeceutically acceptable or pharmaceutically acceptable salt thereof, wherein:

Q is naphthalenyl, quinolinyl, isoquinolinyl, cinnolinyl, phthalazinyl, quinazolinyl, or naphthyridinyl.

3. The compound of claim 2, wherein the compound is of formula (Ib):

(Ib)

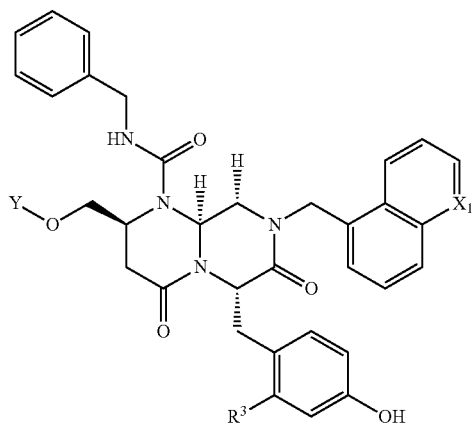

or a cosmeceutically acceptable or pharmaceutically acceptable salt thereof, wherein:

$X_1$ is CH or N;

Y is H or C(O)R;

R is:

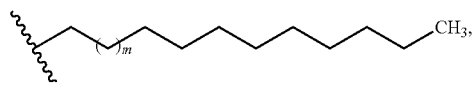

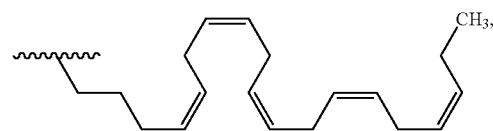

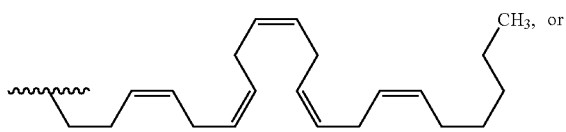

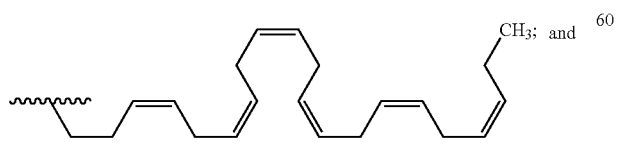

m is 1, 2, 3, 4, 5, 6, 7, 8, 9, or 10.

4. The compound of claim 2, wherein the compound is of formula (Ic):

(Ic)

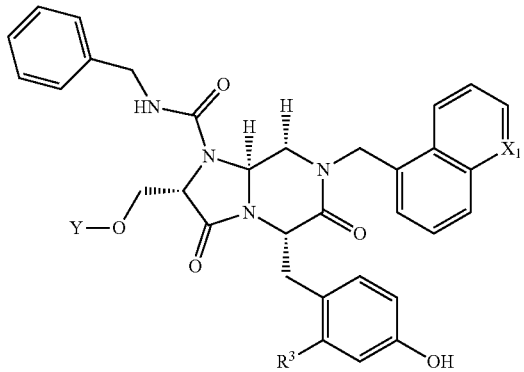

or a cosmeceutically acceptable or pharmaceutically acceptable salt thereof, wherein:

$X_1$ is CH or N;

Y is H or C(O)R;

R is:

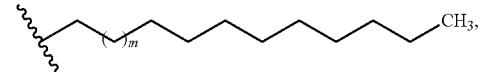

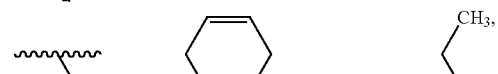

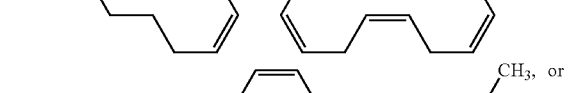

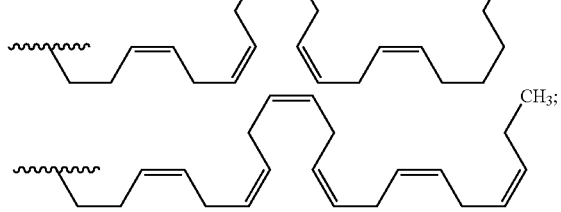

and m is 1, 2, 3, 4, 5, 6, 7, 8, 9, or 10.

5. The compound of claim 1, wherein the compound is selected from the group consisting of:

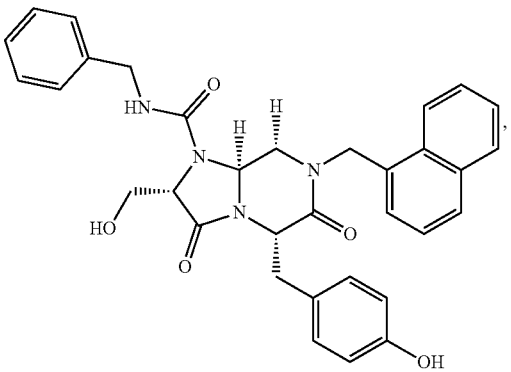

-continued

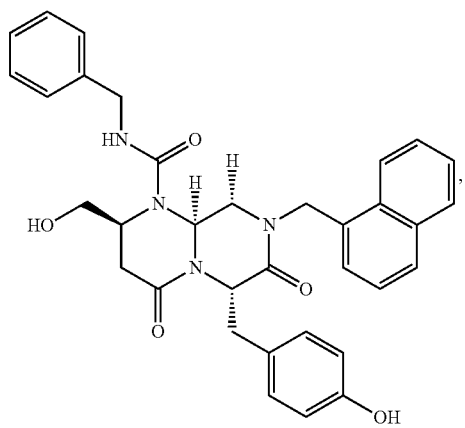

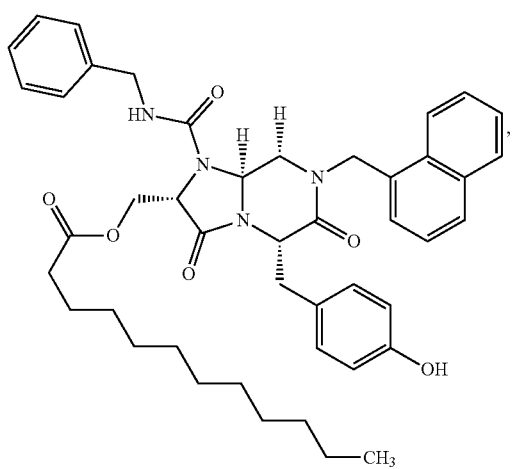

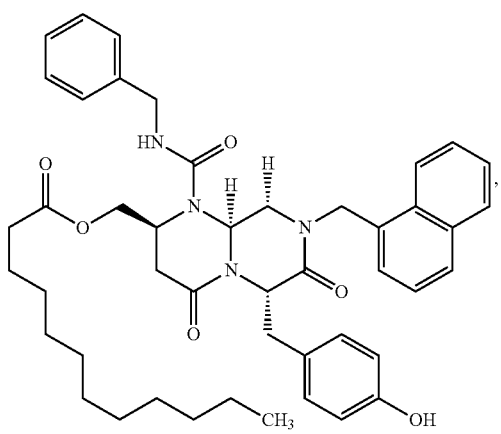

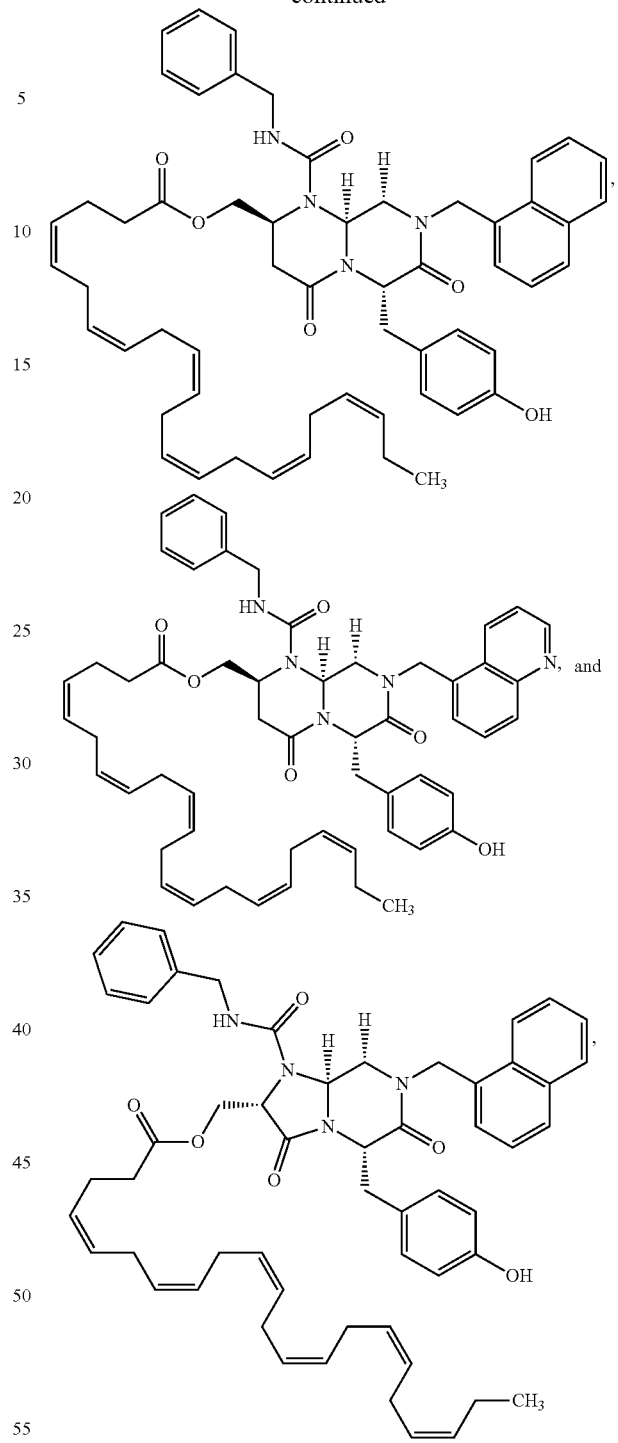

or a cosmeceutically acceptable or pharmaceutically acceptable salt thereof.

6. A cosmeceutical composition comprising a cosmeceutically acceptable excipient and a compound of claim 1, or a cosmeceutically acceptable salt thereof.

7. A pharmaceutical composition comprising a pharmaceutically acceptable excipient and a compound of claim 1, or a pharmaceutically acceptable salt thereof.

8. A method for cosmetically treating a skin condition in a mammalian subject, wherein the method comprises topically administering to the mammalian subject in need thereof a cosmeceutically effective amount of a compound of formula (I):

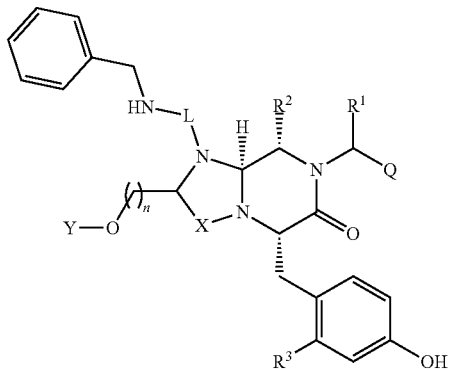

(I)

or a cosmeceutically acceptable salt thereof,
wherein:
L is —C(O)— or —S(O)$_2$—;
X is —C(O)— or —CH$_2$C(O)—;
Y is H or C(O)R;
R is C$_{1-30}$ alkyl or C$_{2-30}$ alkenyl;
R$^1$ is H or CH$_3$;
R$^2$ is H or CH$_3$;
R$^3$ is H or D;
Q is benzyl, phenyl, or an 8- to 11-membered aryl;
wherein the 8- to 11-membered aryl is bicyclic;
wherein the 8- to 11-membered aryl optionally contains 1, 2, or 3 heteroatoms independently selected from the group consisting of nitrogen, oxygen, and sulfur;
wherein the benzyl is optionally substituted with one or more substituents independently selected from the group consisting of halogen, CN, NO$_2$, C$_{1-4}$ perfluoroalkyl, C(NH)NH$_2$, C(O)OH, NH$_2$, NHC$_{1-4}$ alkyl, N(C$_{1-4}$ alkyl)$_2$, NHC(NH)NH$_2$, OH, and OC$_{1-4}$ alkyl; and
wherein the phenyl is optionally substituted with one or more substituents independently selected from the group consisting of halogen, CN, NO$_2$, C$_{1-4}$ alkyl, C$_{1-4}$ perfluoroalkyl, C(NH)NH$_2$, C(O)OH, NH$_2$, NHC$_{1-4}$ alkyl, N(C$_{1-4}$ alkyl)$_2$, NHC(NH)NH$_2$, OH, and OC$_{1-4}$ alkyl; and
n is 1 or 2.

9. The method of claim 8, wherein the skin condition is mediated by cyclic adenosine monophosphate response element binding-binding protein (CBP)/β-catenin signaling.

10. The method of claim 8, wherein the skin condition is an aging skin conditions selected from the group consisting of acne, cracking, dryness, hair loss, hyperpigmentation, loss of elasticity, loss of hair coloration, loss of vibrance, redness, reduced cuticle growth, reduced eyebrow growth, reduced eyelash growth, reduced nail growth, scarring, sun damage, thinning, ultraviolet damage, and wrinkles, or a combination thereof.

11. The method of claim 8, wherein Y is C(O)R.

12. The method of claim 11, wherein:
R is:

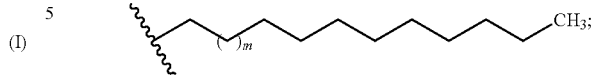

and
m is 1, 2, 3, 4, 5, 6, 7, 8, 9, or 10.

13. The method of claim 8, wherein the compound is of formula (Ia):

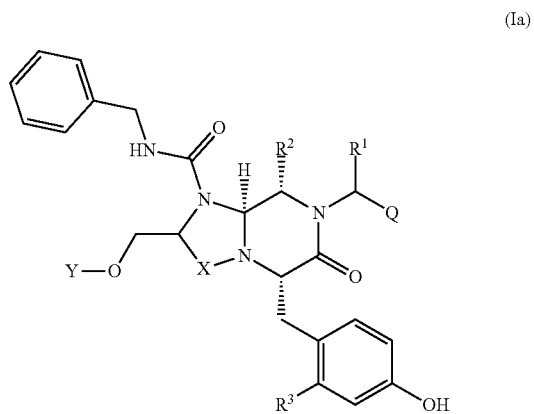

(Ia)

or a cosmeceutically acceptable salt thereof,
wherein:
Q is naphthalenyl, quinolinyl, isoquinolinyl, cinnolinyl, phthalazinyl, quinazolinyl, or naphthyridinyl.

14. The method of claim 13, wherein the compound is of formula (Ib):

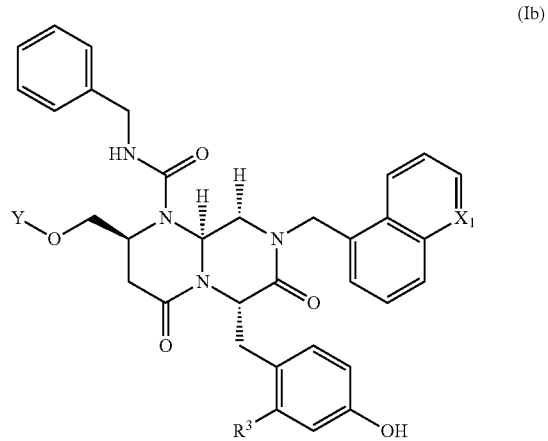

(Ib)

or a cosmeceutically acceptable salt thereof,
wherein:
X$_1$ is CH or N;
Y is H or C(O)R;
R is:

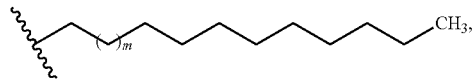

-continued
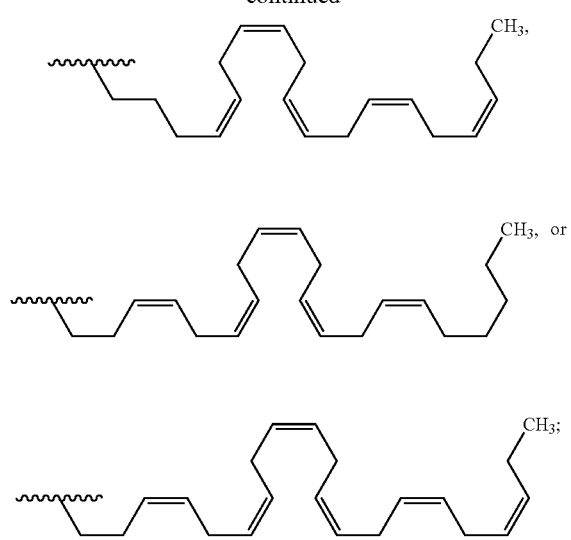
and
m is 1, 2, 3, 4, 5, 6, 7, 8, 9, or 10.
15. The method of claim 13, wherein the compound is of formula (Ic):
(Ic)
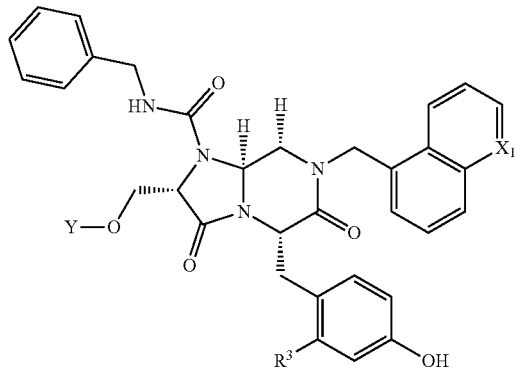
or a cosmeceutically acceptable salt thereof,
wherein:
 $X_1$ is CH or N;
 Y is H or C(O)R;
 R is:
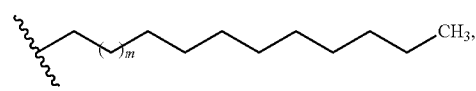
-continued
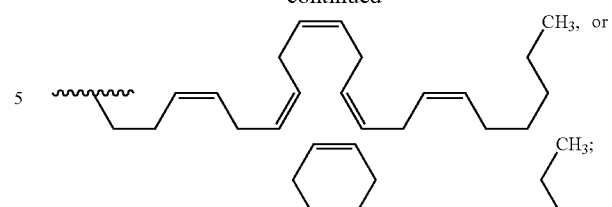
and
m is 1, 2, 3, 4, 5, 6, 7, 8, 9, or 10.
16. The method of claim 8, wherein the compound is selected from the group consisting of:
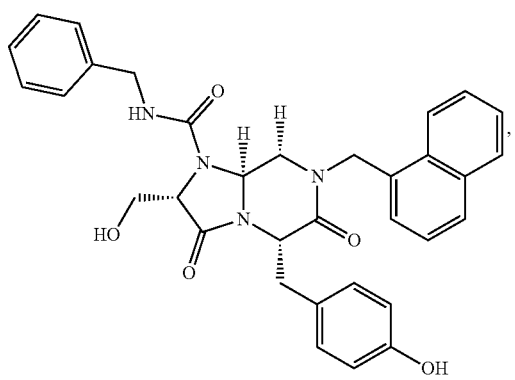
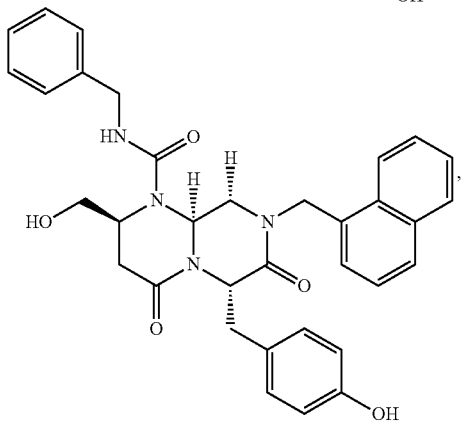
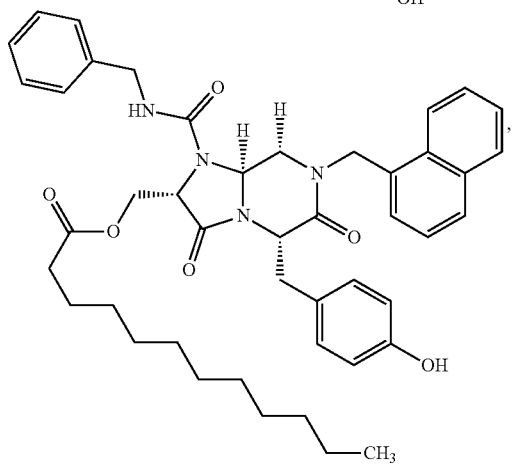

51
-continued

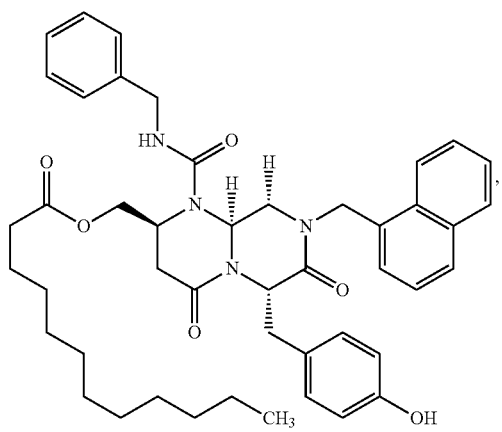

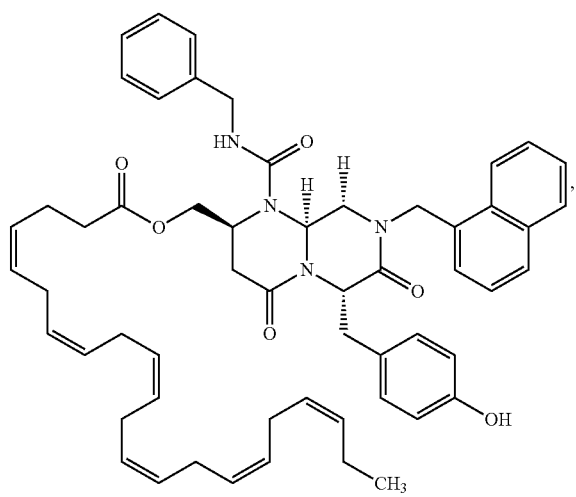

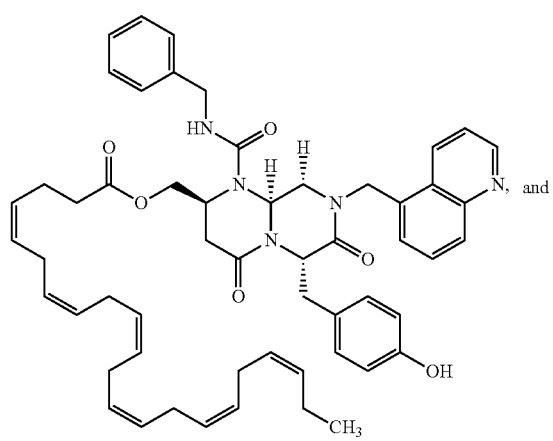

52
-continued

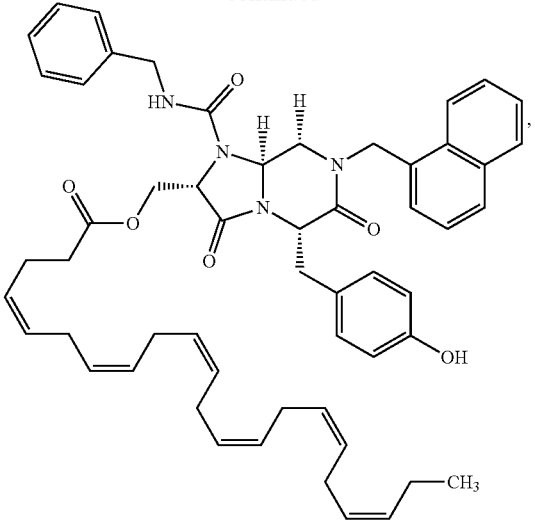

or a cosmeceutically acceptable salt thereof.

17. A method for cosmetically treating a skin condition in a mammalian subject, wherein the method comprises topically administering to the mammalian subject in need thereof a cosmeceutically effective amount of a cosmeceutical composition comprising a cosmeceutically acceptable excipient and a compound of formula (I):

(I)

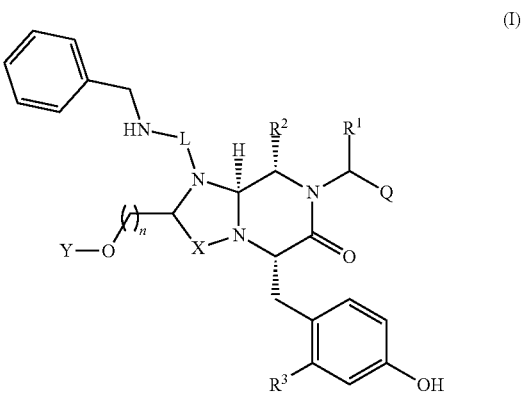

or a cosmeceutically acceptable salt thereof,
wherein:
L is —C(O)— or —S(O)$_2$—;
X is —C(O)— or —CH$_2$C(O)—;
Y is H or C(O)R;
R is C$_{1-30}$ alkyl or C$_{2-30}$ alkenyl;
R$^1$ is H or CH$_3$;
R$^2$ is H or CH$_3$;
R$^3$ is H or D;
Q is benzyl, phenyl, or an 8- to 11-membered aryl;
  wherein the 8- to 11-membered aryl is bicyclic;
  wherein the 8- to 11-membered aryl optionally contains 1, 2, or 3 heteroatoms independently selected from the group consisting of nitrogen, oxygen, and sulfur;
  wherein the benzyl is optionally substituted with one or more substituents independently selected from the group consisting of halogen, CN, NO$_2$, C$_{1-4}$ perfluoroalkyl, C(NH)NH$_2$, C(O)OH, NH$_2$, NHC$_{1-4}$ alkyl, N(C$_{1-4}$ alkyl)$_2$, NHC(NH)NH$_2$, OH, and OC$_{1-4}$ alkyl; and wherein the phenyl is optionally substituted with one or more substituents independently selected from the group consisting of halogen, CN, NO$_2$, C$_{1-4}$ alkyl, C$_{1-4}$ perfluoroalkyl, C(NH)NH$_2$, C(O)OH, NH$_2$, NHC$_{1-4}$ alkyl, N(C$_{1-4}$ alkyl)$_2$, NHC(NH)NH$_2$, OH, and OC$_{1-4}$ alkyl; and n is 1 or 2.

18. The method of claim 17, wherein the skin condition is mediated by cyclic adenosine monophosphate response element binding-binding protein (CBP)/β-catenin signaling.

19. The method of claim 17, wherein the skin condition is an aging skin condition selected from the group consisting of acne, cracking, dryness, hair loss, hyperpigmentation, loss of elasticity, loss of hair coloration, loss of vibrance, redness, reduced cuticle growth, reduced eyebrow growth, reduced eyelash growth, reduced nail growth, scarring, sun damage, thinning, ultraviolet damage, and wrinkles, or a combination thereof.

20. The method of claim 17, wherein Y is C(O)R.

21. The method of claim 20, wherein:

R is:

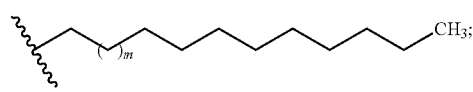

and m is 1, 2, 3, 4, 5, 6, 7, 8, 9, or 10.

22. The method of claim 17, wherein the compound is of formula (Ia):

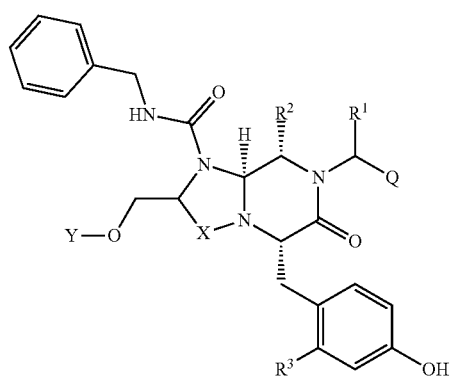

(Ia)

or a cosmeceutically acceptable salt thereof, wherein:

Q is naphthalenyl, quinolinyl, isoquinolinyl, cinnolinyl, phthalazinyl, quinazolinyl, or naphthyridinyl.

23. The method of claim 22, wherein the compound is of formula (Ib):

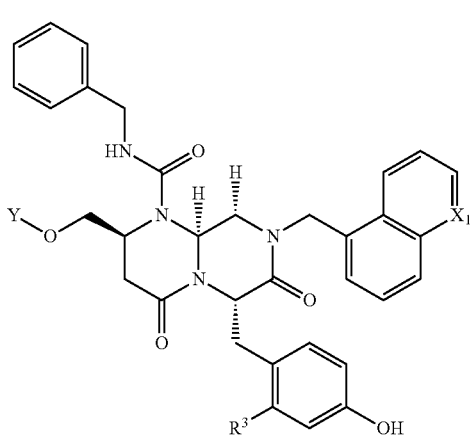

(Ib)

or a cosmeceutically acceptable salt thereof, wherein:

X$_1$ is CH or N;

Y is H or C(O)R;

R is:

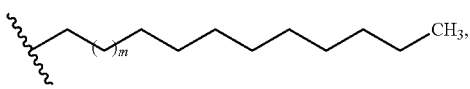

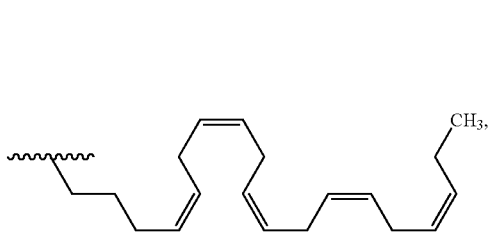

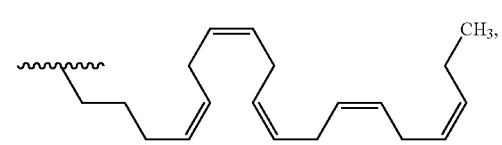

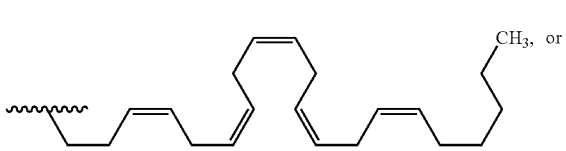

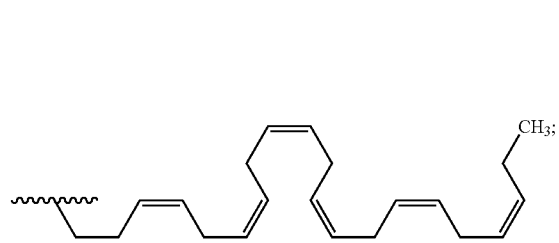

and m is 1, 2, 3, 4, 5, 6, 7, 8, 9, or 10.

24. The method of claim 22, wherein the compound is of formula (Ic):
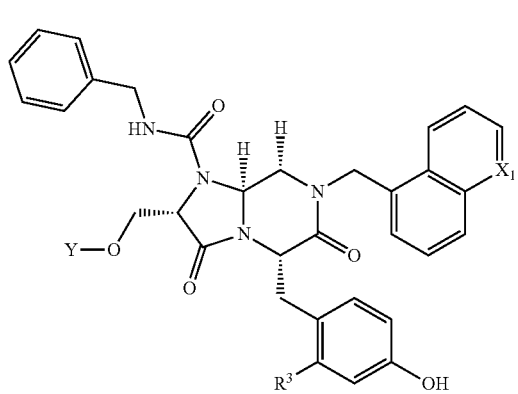
(Ic)
or a cosmeceutically acceptable salt thereof,
wherein:
X$_1$ is CH or N;
Y is H or C(O)R;
R is:
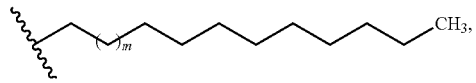
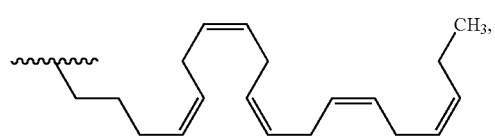
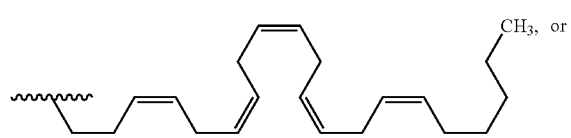
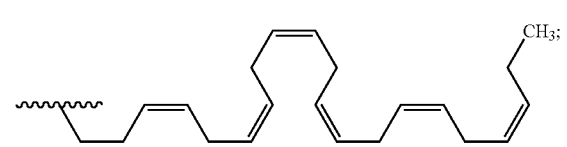
and
m is 1, 2, 3, 4, 5, 6, 7, 8, 9, or 10.
25. The method of claim 17, wherein the compound is selected from the group consisting of:
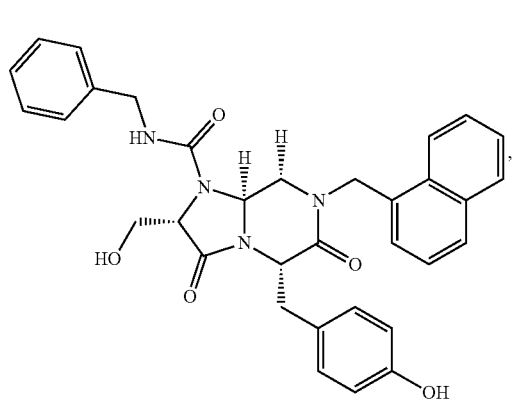
,
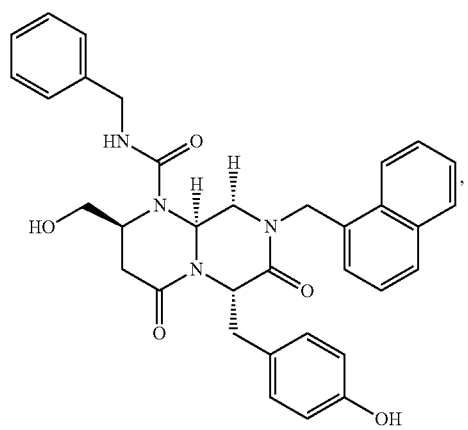
,
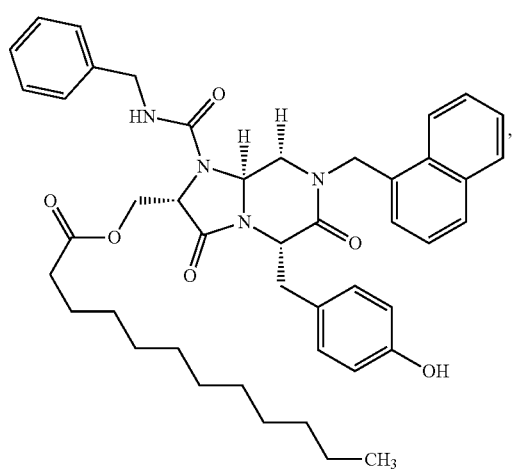
, 57
-continued
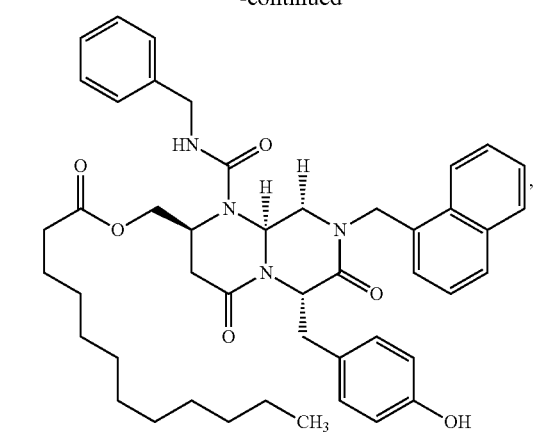
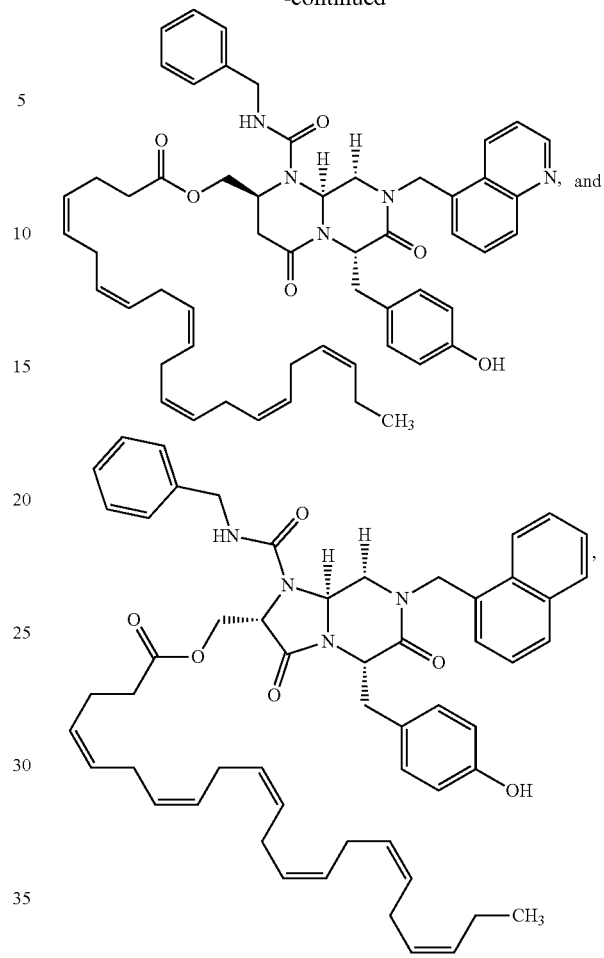
or a cosmeceutically acceptable salt thereof.
* * * * *